US010425355B1

(12) United States Patent
Manoukian et al.

(10) Patent No.: US 10,425,355 B1
(45) Date of Patent: Sep. 24, 2019

(54) DATA STREAM PROCESSING FOR DYNAMIC RESOURCE SCHEDULING

(71) Applicant: HCA Holdings, Inc., Nashville, TN (US)

(72) Inventors: Steven V. Manoukian, Nashville, TN (US); Lindsay Stergar, Nashville, TN (US); Chad Robinson, Nashville, TN (US)

(73) Assignee: HCA Holdings, Inc., Nashville, TN (US)

( * ) Notice: Subject to any disclaimer, the term of this patent is extended or adjusted under 35 U.S.C. 154(b) by 0 days.

(21) Appl. No.: 15/286,397

(22) Filed: Oct. 5, 2016

Related U.S. Application Data

(63) Continuation-in-part of application No. 14/172,736, filed on Feb. 4, 2014, now Pat. No. 9,734,298.

(Continued)

(51) Int. Cl.
*H04L 12/911* (2013.01)
*H04L 29/08* (2006.01)

(52) U.S. Cl.
CPC .......... *H04L 47/827* (2013.01); *H04L 47/78* (2013.01); *H04L 67/10* (2013.01)

(58) Field of Classification Search
CPC ....... H04L 47/827; H04L 47/78; H04L 67/10; H04L 65/607; H04L 65/608; H04L 29/08117; H04L 29/08558; H04L 29/08576; H04L 12/2803; H04L 69/26; H04L 69/28; H04L 69/326; H04L 69/329; H04L 29/0651; H04L 29/06517; H04L 29/0809; H04L 29/08108; G05B 2219/1208; G05B 2219/13121; G05B 2219/23262; G05B 2219/31211; G05B 2219/31324; G05B 19/4185; G05B 19/418; G06F 19/327; G06F 19/3406; G06F 19/322; G06F 19/345; G06F 19/323; G06F 19/3412; G06F 19/3487; G06F 9/46; G06F 15/17331; G06F 17/30017; G06F 17/30368; G06F 17/30551; G06F 17/30873; G06F 19/321; G06F 19/325; G06F 19/326; G06F 19/328; G06F 19/3425; G06F 19/3431; G06F 19/3443; G06F 19/3493;
(Continued)

(56) References Cited

U.S. PATENT DOCUMENTS 6,347,329 B1 2/2002 Evans
7,630,371 B2 * 12/2009 Hernandez ............. G06Q 10/10
370/392
(Continued)

OTHER PUBLICATIONS

U.S. Appl. No. 14/172,736, filed Feb. 4, 2014, Non-Final Office Action dated Aug. 10, 2016, all pages.
(Continued)

*Primary Examiner* — Greg C Bengzon
(74) *Attorney, Agent, or Firm* — Kilpatrick Townsend & Stockton, LLP

(57) ABSTRACT

In some examples, a data stream processing system is provided for processing data streams so as to extract and transmit pertinent information from the data streams to devices or systems. More specifically, the data stream processing system can facilitate a selective, reliable and efficient processing of data elements within the data streams.

20 Claims, 16 Drawing Sheets

Related U.S. Application Data

(60) Provisional application No. 61/760,575, filed on Feb. 4, 2013.

(58) Field of Classification Search
CPC .... G06F 21/602; G06F 21/6245; G06F 21/84; G06F 3/013; G06F 3/015; G06F 3/04817; G06F 3/0482; G06F 17/40; G06F 19/32; G06F 19/34; G06F 19/3418; G06Q 10/10; G06Q 50/24; G06Q 10/107; G06Q 10/00; G06Q 50/22; H04W 84/18; H04W 12/04; H04W 12/06; H04W 48/18; H04W 4/001; H04W 4/006; H04W 4/008; H04W 4/02; H04W 4/028; H04W 4/18; H04W 4/20; H04W 72/02; H04W 76/007; H04W 84/22; H04W 88/04; A61B 5/0022; A61B 5/0002; A61B 5/747; A61B 5/002; A61B 5/1113; A61B 5/4836; A61B 5/746
See application file for complete search history.

(56) References Cited

U.S. PATENT DOCUMENTS

| | | | | |
|---|---|---|---|---|
| 8,165,893 B1* | 4/2012 | Goldberg | G06Q 40/08 | 705/2 |
| 8,825,786 B1* | 9/2014 | Webb, III | G06F 19/3425 | 370/310 |
| 9,560,119 B2* | 1/2017 | Udupi | H04L 67/10 | |
| 2002/0016719 A1* | 2/2002 | Nemeth | G06Q 50/22 | 705/2 |
| 2002/0116453 A1* | 8/2002 | Todorov | H04L 69/329 | 709/203 |
| 2003/0125609 A1* | 7/2003 | Becker | A61B 5/0002 | 600/300 |
| 2003/0154270 A1* | 8/2003 | Aranda, Jr. | G08B 13/19656 | 709/223 |
| 2004/0243444 A1* | 12/2004 | Steusloff | G06F 3/002 | 705/2 |
| 2004/0267570 A1* | 12/2004 | Becker | A61B 5/00 | 705/2 |
| 2005/0067493 A1* | 3/2005 | Urken | G06Q 10/10 | 235/386 |
| 2005/0144042 A1* | 6/2005 | Joffe | G06Q 50/22 | 705/2 |
| 2005/0242928 A1* | 11/2005 | Kirkeby | G08B 5/22 | 340/286.07 |
| 2006/0100899 A1* | 5/2006 | Tajima | G06F 19/3481 | 705/2 |
| 2006/0129345 A1* | 6/2006 | Parvin | G01N 35/00594 | 702/119 |
| 2006/0154642 A1* | 7/2006 | Scannell, Jr. | A01G 9/02 | 455/404.1 |
| 2006/0271409 A1* | 11/2006 | Rosenfeld | G16H 50/20 | 705/3 |
| 2006/0280181 A1* | 12/2006 | Brailas | G06K 7/10099 | 370/392 |
| 2007/0136743 A1* | 6/2007 | Hasek | G08B 25/085 | 725/33 |
| 2008/0058773 A1 | 3/2008 | John | | |
| 2008/0255880 A1* | 10/2008 | Beller | G06Q 10/00 | 705/3 |
| 2009/0006125 A1* | 1/2009 | Angell | G06Q 50/22 | 705/2 |
| 2009/0037225 A1* | 2/2009 | Burchianti, II | G06F 19/327 | 705/3 |
| 2009/0058635 A1* | 3/2009 | LaLonde | A61N 1/37282 | 340/539.11 |
| 2009/0063187 A1* | 3/2009 | Johnson | A61B 5/0022 | 705/2 |
| 2009/0146822 A1* | 6/2009 | Soliman | A61B 5/0002 | 340/573.1 |
| 2009/0216558 A1* | 8/2009 | Reisman | G06F 19/328 | 705/3 |
| 2009/0248828 A1* | 10/2009 | Gould | G08B 27/005 | 709/207 |
| 2009/0259495 A1* | 10/2009 | Rosenfeld | A61B 5/0205 | 705/3 |
| 2010/0004948 A1* | 1/2010 | Toomey | G06F 19/3481 | 705/3 |
| 2010/0169142 A1 | 7/2010 | Hinton et al. | | |
| 2010/0198755 A1* | 8/2010 | Soll | G06F 19/324 | 706/11 |
| 2010/0222649 A1 | 9/2010 | Schoenberg | | |
| 2010/0235187 A1* | 9/2010 | Firminger | G06Q 10/06 | 705/2 |
| 2010/0250271 A1* | 9/2010 | Pearce | G06Q 10/06 | 705/2 |
| 2010/0295685 A1* | 11/2010 | Parvin | G06Q 50/22 | 340/573.1 |
| 2011/0001605 A1* | 1/2011 | Kiani | G06F 19/327 | 340/5.6 |
| 2011/0004491 A1* | 1/2011 | Sameh | G06F 19/322 | 705/3 |
| 2011/0105854 A1* | 5/2011 | Kiani | G06F 19/327 | 600/300 |
| 2011/0172550 A1* | 7/2011 | Martin | A61B 5/7445 | 600/523 |
| 2011/0288877 A1* | 11/2011 | Ofek | G06F 19/322 | 705/2 |
| 2011/0295078 A1* | 12/2011 | Reid | G06Q 50/22 | 600/300 |
| 2011/0295961 A1* | 12/2011 | Wilkes | G06Q 50/24 | 709/206 |
| 2012/0004924 A1* | 1/2012 | Kachnowski | G06F 19/3481 | 705/2 |
| 2012/0004925 A1* | 1/2012 | Braverman | G06F 19/325 | 705/2 |
| 2012/0011125 A1* | 1/2012 | Bousamra | A61B 5/0002 | 707/740 |
| 2012/0117268 A1* | 5/2012 | Shaffer | H04L 45/24 | 709/238 |
| 2012/0209625 A1* | 8/2012 | Armstrong | G06F 19/326 | 705/3 |
| 2012/0215560 A1* | 8/2012 | Ofek | G06F 19/322 | 705/3 |
| 2012/0226796 A1* | 9/2012 | Morgan | H04L 12/1453 | 709/224 |
| 2012/0286953 A1* | 11/2012 | Bousamra | G06F 19/3481 | 340/540 |
| 2012/0316911 A1* | 12/2012 | Schwarz | G06Q 10/10 | 705/7.19 |
| 2013/0024382 A1* | 1/2013 | Dala | G06F 19/322 | 705/51 |
| 2013/0041686 A1* | 2/2013 | Prywes | G06Q 50/22 | 705/3 |
| 2013/0045685 A1* | 2/2013 | Kiani | G06F 19/3406 | 455/41.2 |
| 2013/0054467 A1* | 2/2013 | Dala | G06F 19/322 | 705/51 |
| 2013/0080903 A1* | 3/2013 | Barda | H04L 63/0236 | 715/736 |
| 2013/0096649 A1* | 4/2013 | Martin | G06F 19/322 | 607/60 |
| 2013/0150686 A1* | 6/2013 | Fronterhouse | G06F 19/3418 | 600/323 |
| 2013/0151563 A1* | 6/2013 | Addepalli | H04L 67/10 | 707/792 |
| 2013/0179178 A1* | 7/2013 | Vemireddy | G06Q 10/00 | 705/2 |
| 2013/0262135 A1* | 10/2013 | Nichols | G06Q 50/22 | 705/2 |
| 2013/0278414 A1* | 10/2013 | Sprigg | G08B 21/0453 | 340/539.12 |
| 2013/0279497 A1* | 10/2013 | Verma | H04L 69/18 | 370/352 |
| 2013/0304499 A1* | 11/2013 | Rangadass | G06Q 10/06 | 705/2 |

(56) References Cited

U.S. PATENT DOCUMENTS

| | | | | |
|---|---|---|---|---|
| 2014/0012509 | A1* | 1/2014 | Barber | G06F 3/013 702/19 |
| 2014/0012843 | A1* | 1/2014 | Soon-Shiong | G06F 19/18 707/736 |
| 2014/0019157 | A1* | 1/2014 | Nudd | G16H 40/20 705/2 |
| 2014/0085078 | A1* | 3/2014 | Carnes | A61B 5/746 340/539.12 |
| 2014/0085080 | A1* | 3/2014 | Carnes | A61B 5/746 340/539.12 |
| 2014/0135588 | A1* | 5/2014 | Al-Ali | G06F 19/327 600/300 |
| 2014/0222451 | A1* | 8/2014 | Hall | G06F 19/345 705/2 |
| 2014/0278463 | A1* | 9/2014 | Merry | G06F 19/3406 705/2 |
| 2014/0278496 | A1* | 9/2014 | Spencer | G06F 19/327 705/2 |
| 2014/0280678 | A1* | 9/2014 | Nixon | G06F 15/17331 709/213 |
| 2015/0054947 | A1* | 2/2015 | Dawes | H04L 65/607 348/143 |
| 2015/0066529 | A1* | 3/2015 | Lattuca | G06Q 50/22 705/2 |
| 2015/0070187 | A1* | 3/2015 | Wiesner | A61B 5/0022 340/870.02 |
| 2015/0097701 | A1* | 4/2015 | Al-Ali | A61B 5/0002 340/870.07 |
| 2015/0099458 | A1* | 4/2015 | Weisner | H04W 84/22 455/15 |
| 2015/0112696 | A1* | 4/2015 | Kharraz Tavakol | G06Q 10/06311 705/2 |
| 2015/0154528 | A1* | 6/2015 | Kharraz Tavakol | G06F 19/327 705/2 |
| 2015/0341231 | A1* | 11/2015 | Khan | H04L 43/04 709/219 |
| 2016/0004831 | A1* | 1/2016 | Carlson | G06F 19/363 705/2 |
| 2016/0058286 | A1* | 3/2016 | Joshua | A61B 5/0022 340/870.07 |
| 2016/0098525 | A1* | 4/2016 | Maheshwari | G06F 19/327 705/2 |
| 2016/0157113 | A1* | 6/2016 | Row, II | H04W 84/18 370/252 |
| 2016/0182614 | A1* | 6/2016 | Udupi | H04L 67/10 709/217 |
| 2016/0321406 | A1* | 11/2016 | Timmerman | G06F 19/326 |
| 2016/0360466 | A1* | 12/2016 | Barak | H04W 8/26 |
| 2017/0109479 | A1* | 4/2017 | Vemireddy | G06F 19/00 |
| 2018/0174680 | A1* | 6/2018 | Sampath | G06F 19/3418 |

OTHER PUBLICATIONS

U.S. Appl. No. 14/172,736, filed Feb. 4, 2014, Final Office Action dated Jul. 30, 2015, all pages.

U.S. Appl. No. 14/172,736, filed Feb. 4, 2014, Non-Final Office Action dated Dec. 10, 2014, all pages.

U.S. Appl. No. 14/172,736, filed Feb. 4, 2014, Notice of Allowance dated Apr. 12, 2017, all pages.

* cited by examiner

DATA STREAM PROCESSING FOR DYNAMIC RESOURCE SCHEDULING

CROSS-REFERENCE TO RELATED APPLICATIONS

The present application is a continuation-in-part application which claims the priority benefit under 35 USC 119(e) to U.S. Ser. No. 14/172,736, filed on Feb. 4, 2014, which claims priority to U.S. Provisional Application No. 61/760,575, filed on Feb. 4, 2013, the disclosures of each of which are incorporated by reference herein in their entirety for all purposes.

FIELD

This disclosure relates to the processing of data streams. More specifically, application of particular protocols to a stream facilitate a selective, reliable and efficient processing of data elements within the data streams based on composites of the data elements.

BACKGROUND

An increasing amount of data is becoming available to collectively process and use to detect particular events. Though the increased data quantity provides immense power, it also presents difficulties. Capabilities to process massive amounts of stream data and process pertinent information from the stream data may be limited at various systems within a network. Systems may not be suited to effectively process large amounts of stream data from various sources.

SUMMARY

In some embodiments, a stream processing system is provided for processing data streams so as to extract and transmit pertinent information from the data streams to devices or systems. One or more data sources can transmit source data. Source data can include one or more data streams. A stream processor system can receive the source data, and selectively transmit a data stream from the one or more data streams. Each data stream of the one or more data streams can include a plurality of data elements. Each data element of the plurality of data elements can include a parameter composite and a condition composite. A communication facilitation system can, for a data stream of the one or more data streams: parse the data stream into one or more individual data elements, and extract information from a parameter composite and a condition composite of an individual data element of the one or more individual elements. The communication facilitation system can identify a user communication device using the extracted parameter and the extracted additional information, query a lookup table using the condition composite, and identify priority tag based on result of query. Further, the communication facilitation system can associate the identified priority tag to the individual data element and identify a communication protocol associated with the identified priority tag. For example, the communication protocol can include a communication trigger that indicates a target task. In addition, the communication facilitation system can identify a navigator device based on the source data. For example, the navigator device can be associated with a resource scheduling allocation (e.g., a timetable), detect that the communication trigger has occurred based on the resource scheduling allocation, and facilitate an initiation of a communication attempt between the navigator device and the user communication device.

Embodiments of the present disclosure may also include a computer-implemented method. The computer-implemented method can include any combination of operations or all operations performed by any combination of elements or all elements of the system described above and herein.

Embodiments of the present disclosure may also include a computer-program product tangibly embodied in a non-transitory machine-readable storage medium, including instructions configured to cause a data processing apparatus to perform operations including any of the computer-implemented methods and operations described above and herein.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Figure 1:
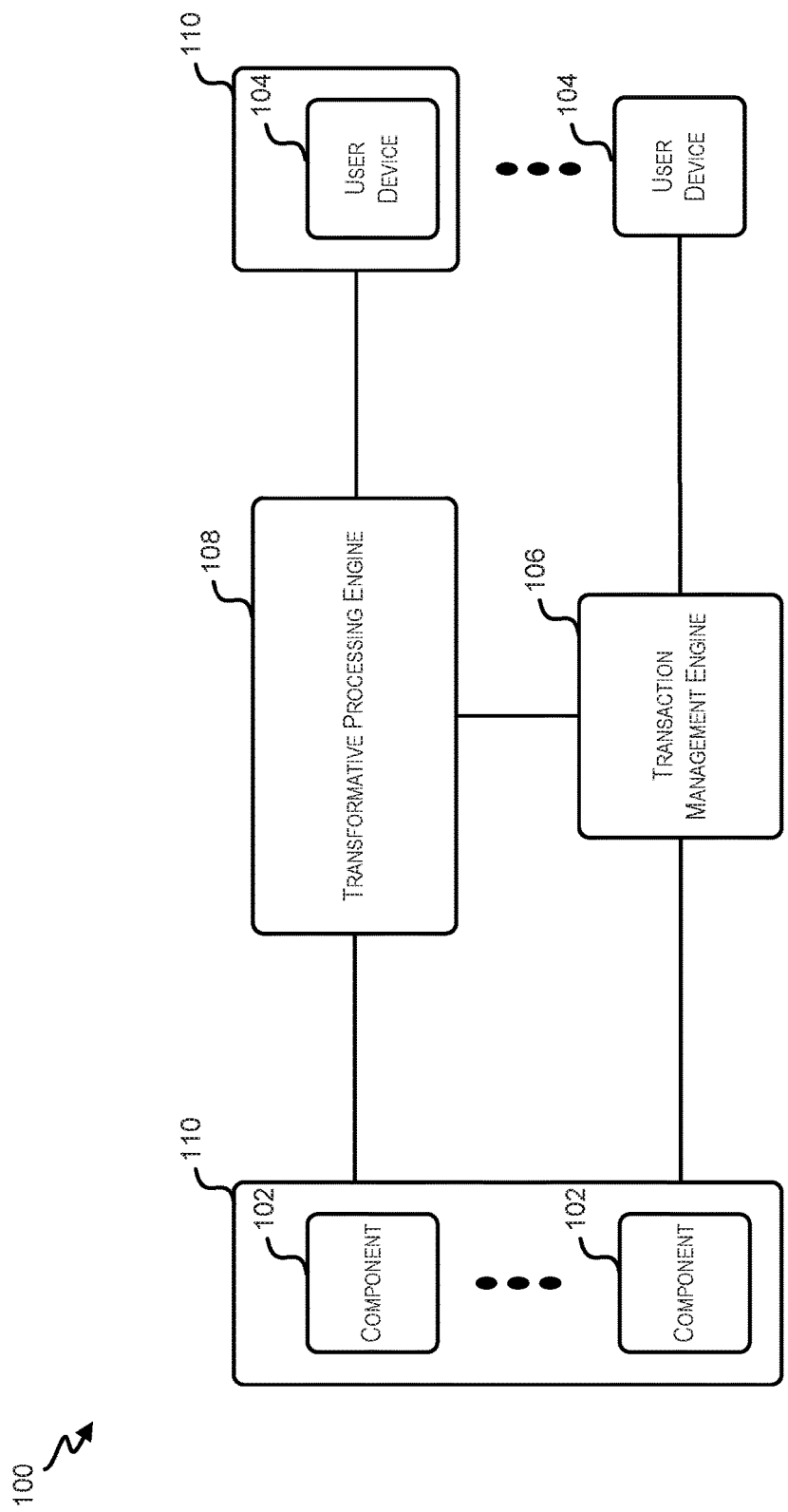
FIG. 1 shows a block diagram of an embodiment of an interaction system.

Referring first to FIG. 1, a block diagram of an embodiment of an interaction system 100 is illustrated. Generally, in interaction system 100, data can be generated at one or more system components 102 and/or user devices 104. Transaction management engine 106 van manage the flow of communications within interaction system. Transformative processing engine 108 can receive, intercept, track, integrate, process and/or store such data.

Data flowing in interaction system 100 can include a set of communications. Each of one, some of all communications can include (for example) an encoding type, authentication credential, indication of a content size, identifier of a source device, identifier of a destination device, identifier pertaining to content in the communication (e.g., an identifier of an entity), a processing or reporting instruction, a procedure specification, transmission time stamp, and/or sensor measurement. Data may, or may not, selectively pertain to a particular entity and/or client. Data can, depending on the implementation, include individually identifiable information and/or de-identified information as it pertains to an entity and/or client. Data may, but need not, include protected information.

For example, a system component 102 can include, for example, a sensor to detect a sensor measurement and can thereafter generate and transmit a communication that reflects the sensor measurement. The communication may be transmitted at routine times and/or upon detecting a threshold (e.g., one or more) number of measurements or a measurement satisfying a transmission condition (e.g., exceeding a threshold value). In some instances, the sensor measurement corresponds to one reflecting a property of an object or entity (e.g., person) near the sensor. The communication may then include an identifier of the object or entity. The identifier can be determined, for example, based on detection of a nearby electronic tag (e.g., RFID tag), a detected user input received at a user interface of component 102 and/or data in a corresponding communication received from a user device.

As another example, a user device 104 can be configured to detect user input received at a user interface of the device. The user input can include, for example, an identifier of an object or entity, an instruction, a characterization of an object or entity, an identification of an assessment to be performed, a specification of an aggregation or data processing to be performed, and/or an identification of a destination for a data-analysis report. User device 104 can further be configured to detect user input requesting particular data, to generate a request communication (e.g., to be sent to transformative processing engine), to receive the requested data and/or to present the received data.

Data can include information that identifies a person, such as personal information and/or demographic information. For example, the information can identify a person's name, age, sex, race, physical address, phone number, email address and/or social security number. Data may include information collected by a government agent, employer, insurer, or school or university, that relates to a past, present, or future condition or status (e.g., pertaining to employment, political involvement, or occupation, etc.) of any individual. For example, data may include information about past events.

Data may identify an entity being evaluated and/or one at least partly performing an evaluation. For example, a communication may identify a first company as one being evaluated and a second company as one evaluating a quality of a product of the first company. As another example, a communication may identify a first service plan of a first company as one providing an Internet network and may identify one or more users providing speed checks over the network.

The depicted engines, devices and/or components can communicate over one or more networks. A network of one or more networks can include a wired network (e.g., fiber, ethernet, powerline ethernet, ethernet over coaxial cable, digital signal line (DSL), or the like), wireless network (e.g., Zigbee™, Bluetooth™, WiFi™, IR, UWB, WiFi-Direct, BLE, cellular, Long-Term Evolution (LTE), WiMax™, or the like), local area network, the Internet and/or a combination thereof. It will be appreciated that, while one or more components 102 and one or more user devices 104 are illustrated as communicating via transformative processing engine 108 and/or transaction management engine 106, this specification is not so limited. For example, each of one or more components 102 may communicate with each of one or more user devices 104 directly via other or the same communication networks.

A component 102 can be configured to detect, process and/or receive data, such as environmental data, geophysical data, biometric data, chemical data (e.g., chemical composition or concentration analysis data), and/or network data. The data can be based on data detected, for example, via a sensor, received signal or user input. A user device 104 can include a device configured to receive data from a user and/or present data to a user. It will be appreciated that, in some instances, a component 102 is also a user device 104 and vice-versa. For example, a single device can be configured to detect sensor measurements, receive user input and present output.

A component 102 can be configured to generate a communication that is in one or more formats, some of which can be proprietary. For example, an imaging machine (e.g., one of one or more components 102) manufactured by company A, located within a first facility (e.g., facility 110), and belonging to a first client, may save and transfer data in a first format. An imaging machine (e.g., one of one or more components 102) manufactured by company B, located within the first facility (e.g., facility 110), and belonging to the first client, may save and transfer data in a second format. In some examples, data from certain components is transformed, translated, or otherwise adjusted to be recognizable by transformative processing engine 108. Thus, continuing with the example from above, when the imaging machines manufactured by companies A and B are located within the first facility belonging to the first client, they may nevertheless save and transfer data in different formats. In some examples, one or more components 102 communicate using a defined format.

In some examples, each of one or more components 102 are each associated with one or more clients within a same or different interaction systems. For example, certain ones of one or more components 102 may be associated with a first client, while other ones of one or more components 102 may be associated with a second client. Additionally, each of one or more components 102 may be associated with a facility 110 (e.g., client facility). Each facility 110 may correspond to a single location and/or processing focus. Exemplary types of facilities include server farm facilities, web-server facilities, data-storage facilities, technical-support facilities, telecommunication facilities, care facilities and/or business operation facilities. For example, a first facility may include a structure at a first location at which one or more resources (e.g., computational resources, equipment resources, laboratory resources and/or human resources) are provided. Each of the one or more resources may be of a first type in a first set of types. A resource type can be identified based on, for example, a characteristic of the resource (e.g., sensor inclusion) and/or a capability of providing each of one or more services. Thus, for example, resources at a first facility may be better configured for handling a particular type of service requests compared to those in another facility. As another examples, different facilities may include resources of similar or same types but may vary in terms of, for example, user accessibility, location, managing client, etc.

Transmission of data from one or more components 102 to transformative processing engine 108 may be triggered by a variety of different events. For example, the data may be transmitted periodically, upon detection of an event (e.g., completion of an analysis or end of a procedure), upon detection of an event defined by a rule (e.g., a user-defined rule), upon receiving user input triggering the transmission, or upon receiving a data request from transformative processing engine 108. Each transmission can include, e.g., a single record pertaining to a single entity, object, procedure, or analysis or multiple records pertaining to multiple entities, objects, procedures, or analyses.

In some examples, at least some of one or more user devices 104 are associated with facility 110. In some examples, at least some of one or more user devices 104 need not be associated with facility 110 or any other facility. Similar to one or more components 102, one or more user devices 104 may be capable of receiving, generating, processing and/or transmitting data. Examples of one or more user devices 104 include, for example, a computer, a mobile device, a smart phone, a laptop, an electronic badge, a set-top box, a thin client device, a tablet, a pager, and other similar user devices). One or more user devices 104 may be configured to run one or more applications developed for interacting with data collected by transformative processing engine 108. For example, those user devices of one or more user devices 104 that are not associated with facility 110 may be configured to run one or more third-party applications that may rely in part on the data gathered by transformative processing engine 108.

Each of one or more components 102 and one or more user devices 104 may be utilized by one or more users (not shown). Each of the one or more users may be associated with one or more clients. For example, one of the one or more users can be associated with a client as a result of being employed by the client, physically located at a location of the client, being an agent of the client or receiving a service from the client.

In some examples, one or more components 102 and one or more user devices 104 may communicate with transformative processing engine 108 and transaction management engine 106 via different information formats, different proprietary protocols, different encryption techniques, different languages, different machine languages, and the like. As will be discussed with reference to FIG. 2, transformative processing engine 108 is configured to receive these many different communications from one or more components 102, and in some examples from one or more user devices 104, in their native formats and transform them into any of one or more formats. The received and/or transformed communications can be transmitted to one or more other devices (e.g., transaction management engine 106, an entity device and/or a user device) and/or locally or remotely stored. In some examples, transformative processing engine 108 receives data in a particular format (e.g., the HL7 format) or conforming to any other suitable format and/or is configured to transform received data to conform with the particular format.

One or more components 102 of facility 110 can include and/or has access to a local or remote memory for storing generated data. In some examples, the data is stored by one or more servers local to facility 110. Such storage may enable facility 110 to retain locally data pertaining to its facility prior to (or in conjunction with) the data being shared with transformative processing engine 108 and/or transaction management engine 106. In some examples, the one or more servers of facility 110 share data directly with a record service (not shown), and the record service makes the data available to transformative processing engine 108 and/or transaction management engine 106. Once an electronic record is updated at facility 110, an indication of the update may be provide to the record service. The record service may then update a corresponding record associated with the electronic record.

The record service can be granted access to the data generated and/or transmitted by one or more components 102. In some examples, the record service includes a server or a plurality of servers arranged in a cluster or the like. These server(s) of the record service can process and/or store data generated by one or more components 102. For example, one or more records can be generated for each entity (e.g., each record corresponding to a different entity or being shared across entities). Upon receiving a communication with data from an component (or facility), the record service can identify a corresponding record and update the record to include the data (or processed version thereof). In some examples, the record service provides data to transformative processing engine 108.

Facility 110 can include one at which a resource is located and/or service is provided. Irrespective of the type of facility, facility 110 may update data, maintain data, and communicate data to transformative processing engine 108. At least some of the data may be stored local to facility 110.

A user interacting with a user device 104 can include, for example, a client customer, client agent and/or a third party. A user may interact with user device 104 and/or component 102 so as to, for example, facilitate or initiate data collection (e.g., by a component 102), provide data, initiate transmission of a data request, access data and/or initiate transmission of a data-processing or data-storage instruction. In some instances, one or more user devices 104 may operate according to a private and/or proprietary network or protocols. In other examples, one or more user devices 104 may operate on public networks. In any case, however, transformative processing engine 108 can have access to the one or more components and can communicate with them via a public, private and/or proprietary network or protocols. The use of one or more private and/or proprietary protocols can promote secure transfer of data.

Figure 2:
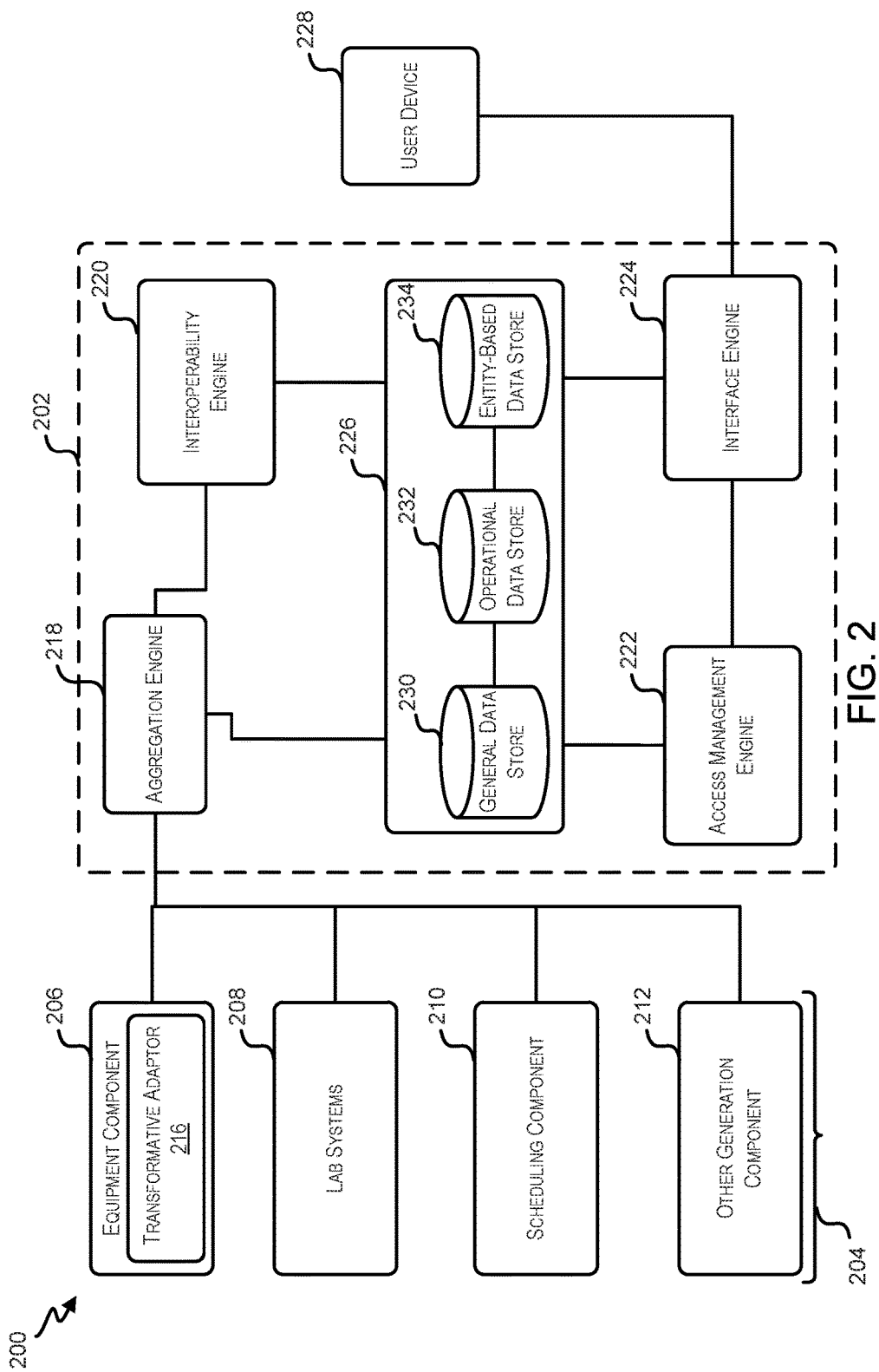
FIG. 2 shows a block diagram of an example of an interaction system.

Referring next to FIG. 2, a block diagram of an example of an interaction system 200 is shown. Interaction system 200 includes a transformative integration engine 202. Transformative integration engine 202 is an example of transformative processing engine 108 discussed with reference to FIG. 1. Interaction system 200 also includes one or more generation components 204. In particular, one or more generation components 204 includes an equipment component 206, a lab systems component 208, a scheduling component 210 and other generation component 212. One or more generation components 204 are examples of one or more components 102 discussed with reference to FIG. 1.

Generally, one or more generation components 204 includes any suitable device or system capable of generating data in the context of an interaction system. For example, the other generation component 212 may include a sensor on a door, and equipment component 206 may include a sophisticated computer-controlled laser device. In either case, each generation component generates some type of data. For example, the data provided by the sensor may be used to address security concerns or assessing heating, ventilating, and air conditioning (HVAC) costs for an institution. The data provided by the laser device may have been provided while engaged in a procedure and may then be used by other entities in the future to decide how to use the device.

As discussed in further detail herein, data generated by one or more generation components 204 can be of a variety of formats, some of which may be proprietary. For example, a single component can generate data in multiple formats, different components can generate data in different formats, and/or different component types can result in generation of data in different formats. In some instances, formatting of a data can depend on a service having been provided, a user initiating data generation, a destination to receive the data, a location at which a service was provided, etc. In some examples, a typical interaction system includes thousands of generation components producing data in hundreds of formats. In order to harness the power that comes from such a large amount of data to make informed decisions, it is desirable that all, or at least a large portion of the data, is shared. Use of transformative integration engine 202 in accordance with techniques described herein may achieve this design—making large amounts of data, in many different originating formats available to various types of users, via one or more interfaces.

While one or more generation components 204 are illustrated adjacent to each other, it is understood that each may be located within one facility or that the components may be spread out among many facilities. In addition, in some examples, one or more generation components 204 belong to different clients.

Turning now to equipment component 206, this component includes any machine, contrivance, implant, or other similar related article, that is intended to aid in reaching a particular objective. In some instances, equipment component 206 includes one or more sensors to detect environmental or other stimuli. Equipment component 206 can include, for example, equipment to monitor a stimulus, detect stimulus changes, detect stimulus-indicative values, and so on. Exemplary equipment components 206 include an imaging device, a device that detects and characterizes electrical signals, a device that detects pressure, and/or a device that detects concentration of one or more particular elements, compounds and/or gases.

As illustrated, equipment component 206 includes transformative adaptor 216. In some examples, transformative adaptor 216 is a device that transforms, translates, converts, or otherwise adjusts output data from equipment component 206. For example, an equipment component 206 can be a scanner that outputs its results in format A, but the majority of other scanners in the interaction system output their results in format B. Transformative adaptor 216 may be implemented to convert or otherwise adjust the results in format A to conform closer to format B. For example, the conversion from format A to format B may be performed using a conversion rule, which may be user-define or learned. Transformative integration engine 202 may perform similar tasks as it relates to all data generated within interaction system 200. In this manner, transformative adaptor 216 can perform an initial step in the process of transformation, translation, conversion, or adjustment of the output of equipment component 206. In some examples, transformative adaptor 216 is implemented in hardware, software, or any suitable combination of both. In some examples, other transformative adaptors (not shown) may be implemented within others of one or more generation components 204. In some examples, equipment component 206 may not include transformative adaptor 216.

Lab systems component 208 includes any suitable laboratory equipment or system that is intended to analyze material, such as biological material. This includes, for example, laboratory equipment that analyzes biological samples; electric microscopes; ultracentrifuges; data collection devices, including Kymographs, sensors connected to a computer to collect data; monitoring devices; computers used to report results of lab tests, and other similar laboratory equipment. Each of the above-listed components generates data that is provided (directly or indirectly) to transformative integration engine 202.

Scheduling component 210 includes any suitable computing devices used for business-related purposes with respect to interaction system 200. For example, scheduling component 210 can be configured to schedule a resource for allocation for a particular entity during a particular time slot. Scheduling component 210 can monitor a schedule for the resource and can identify one or more available time slots that may be secured by a particular entity. Upon receiving a scheduling indication, scheduling component 210 may update a schedule of a resource to reflect that a particular time slot is to be allocated for service of a particular entity.

Each of one or more generation components 204 and the user device 228 may include individual and/or shared storage systems, one or more processors, a user interface, a network connectivity device, and one or more ports. The storage system include memory that may be implemented, e.g., using magnetic storage media, flash memory, other semiconductor memory (e.g., DRAM, SRAM), or any other non-transitory storage medium, or a combination of media, and can include volatile and/or non-volatile media. The storage systems may also be configured to store computer-executable code or instructions for interacting with the user interface and/or for one or more applications programs, such as an application program for collecting data generated by the particular generation component.

The one or more processors may be configured to access the operating system and application programs stored within the storage systems, and may also be configured to execute such program code. The one or more processors can be implemented as one or more integrated circuits, e.g., one or more single-core or multi-core microprocessors or microcontrollers, examples of which are known in the art. In operation, the one or more processors can control the operation of the particular component. The one or more processors may access and execute the program code and at any given time.

The user interface can include any combination of input and output devices. In some instances, a user can operate input devices of the user interface to invoke the functionality of the particular component or user device. For example, the user interface may enable the user to view, hear, and/or otherwise experience output from component or user device via the output devices of the user interface. Examples of output devices include a display, speakers, and the like.

The network connectivity device may enable the component or user device to communicate with transformative integration engine 202 and other components or other user devices via one or more networks. The one or more networks may include any suitable combination of cable, cellular, radio, digital subscriber line, or any other suitable network, which may be wired and/or wireless. In some examples, the network connectivity device may enable the component or the user device to communicate wirelessly with various other components and/or transformative integration engine 202. For example, the components may include circuitry to enable data communication over a wireless medium, e.g., using near-field communication (NFC), Bluetooth Low Energy, Bluetooth® (a family of standards promulgated by Bluetooth SIG, Inc.), Zigbee, Wi-Fi (IEEE 802.11 family standards), or other protocols for wireless data communication.

The one or more ports may enable the component or the user device to receive data from one or more sensors. The sensors may be any suitable type of sensor to capture data. Such captured data may be shared with transformative integration engine 202 in accordance with techniques described herein. In some examples, the sensors may also be configured to detect the component's or the user device's location and other details about the component or the user device. In some examples, the component and user device may include global positioning chips for determining a geolocation. Such geolocation information may be relevant to analyzing the data provided by the component or the user device located at the geographic location.

Transformative integration engine 202 includes an aggregation engine 218, an interoperability engine 220, an access management engine 222, an interface engine 224, and a data store 226. Generally aggregation engine 218 is configured to collect data from multiple communications. The data may be from one or multiple generation components 204 and/or may be of a same or different formats. Aggregation engine 218 may be configured to perform one or more operations on the collected data. For example, aggregation engine 218 may tag data, log data, perform protocol conversion, and may support one-to-many communications. The collection may be asynchronous. In some examples, the data has been saved locally in connection with one or more generation components 204 in many different formats having many different data structures.

Aggregation engine 218 can identify data to be aggregated based on, for example, intra-communication data, a current time, a source generation component, and/or one or more aggregation rules. For example, an aggregation rule may specify that data is to be aggregated across all communications that include content with a same entity identifier. An aggregation may be dynamic. For example, aggregated data may reflect that from within a most recent 12-hour period. Thus, an aggregation may be updated in time to exclude older data from the aggregation and to include newer data.

Aggregation engine 218 can be configured to provide data from one or more communications to interoperability engine 220. Interoperability engine 220 can be configured to perform one or more operations on the received data and store it in data store 226. For example, interoperability engine 220 may perform semantic tagging and indexing of data. This may include extracting field values from data, categorizing data (e.g., by type of data, characteristic of an entity, location of facility, characteristic of facility, and the like), anonymizing or partially-anonymizing data, and the like. Interoperability engine 220 may also include a high availability cache, an alerts engine and a rules engine. In some examples, interoperability engine 220 operates synchronously.

From interoperability engine 220, data flows to data store 226. Data store 226 (and any other data store discussed herein) may include one or more data stores, which may be distributed throughout two or more different locations (e.g., present on different devices, which can include devices of different entities and/or a cloud server). In some examples, data store 226 includes a general data store 230, an operational data store 232, and an entity-based data store 234. Within each of the data stores 230, 232, and 234 is stored data. Depending on the structure of the particular data store, certain data stores may include rules for reading and writing. The data stores 230, 232, and 234 may include records, tables, arrays, and the like, which may be relational or non-relational. Depending on the data store, records for individual entities, business and analytics information, output data from one or more generation components 204, and the like may be retained. The data within the data stores 230, 232, and 234 include elements or tags such that a particular data (e.g., for a single entity, protocol, etc.) can be retrieved.

Access management engine 222 is configured to manage access to features of transformative integration engine 202, including access to the data retained in data store 226. For example, access management engine 222 may verify that a user device such as user device 228 is authorized to access data store 226. To verify the user device 228, access management engine 222 may require that a user of the user device 228 input a username and password, have a profile associated with the interaction system, have paid a subscription fee associated with access to data store 226, and the like. Access management engine 222 may also verify that the user device 228 has an IP address or geographical location that corresponds to an authorized list, that the user device 228 includes a plug-in for properly accessing data store 226, that the user device 228 is running certain applications required to access data store 226, and the like.

Interface engine 224 is configured to retrieve the data from data store 226 and provide one or more interfaces for interacting with elements of transformative integration engine 202. For example, interface engine 224 includes an interface by which an application running on user device 228 can access portions of data within data store 226.

Figure 3:
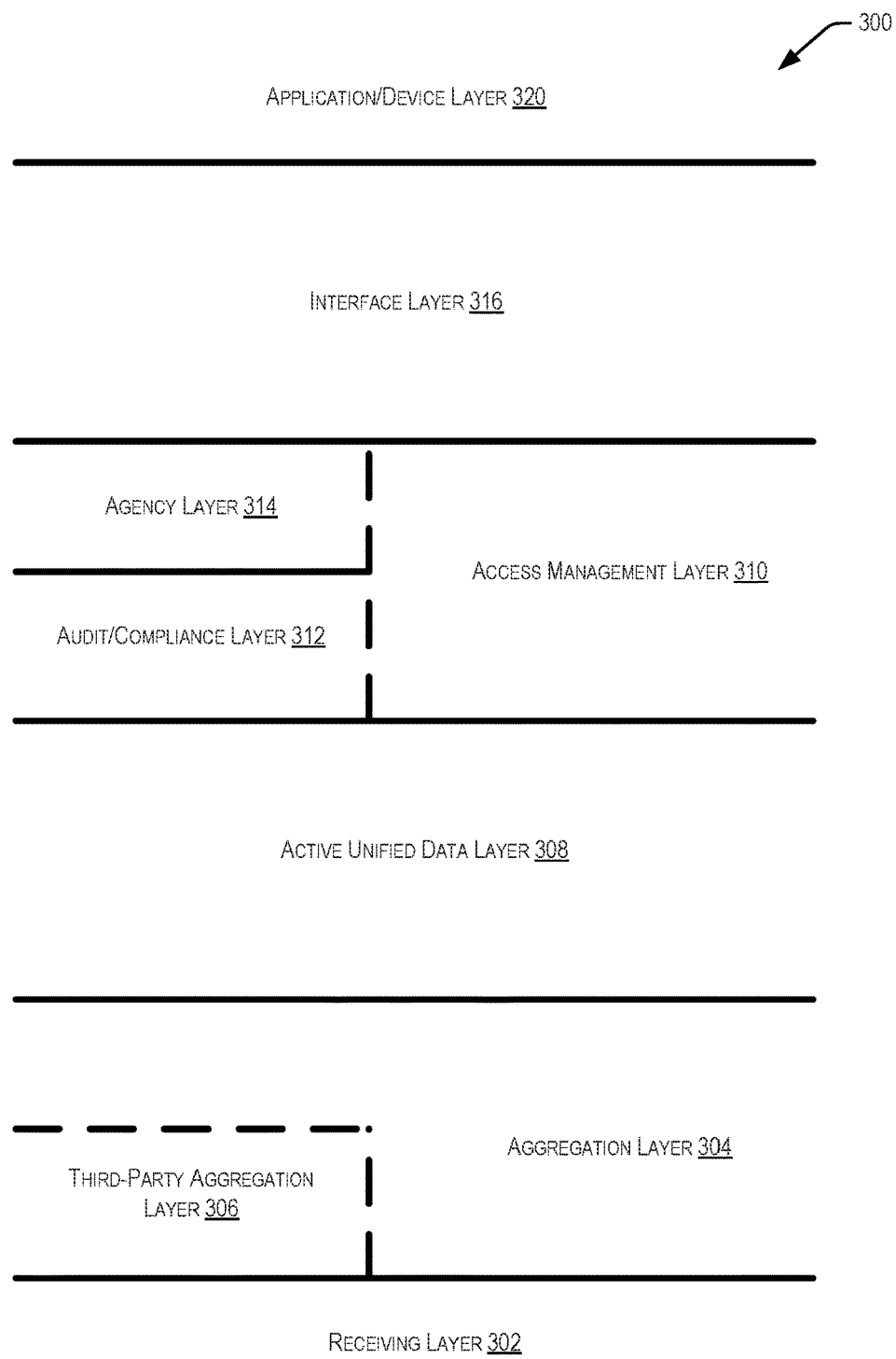
FIG. 3 shows an architecture stack according to an embodiment of the invention.

Turning next to FIG. 3, an architecture stack 300 is shown. In some examples, techniques relating management of data are implemented in accordance with architecture stack 300. And while architecture stack 300 is illustrated as having a particular structure, it is understood that other structures, including those with more or less layers than illustrated, is within the scope of this specification. In some examples, architecture stack 300 is implemented across an interaction system having a plurality of systems belonging to the same client or spread across different clients. Thus, architecture stack 300 can be used to integrate different systems of different organizations, entities, and the like and to provide a fluid sharing of information among elements within the interaction system and without the interaction system. In some instances, a multi-layer part of architecture stack 300 is implemented at a single system or device within an interaction system.

The different layers of architecture stack 300 will be described generally with reference to FIG. 3 and in detail with reference to subsequent figures. Architecture stack 300 includes a receiving layer 302 as the bottom-most layer. Receiving layer 302 includes receiving data from elements that share data with other elements within an aggregation layer 304. For example, as detailed herein, receiving layer 302 can include receiving data from generation components that generate data. As such, receiving layer 302 is where data that has been created is received. In some examples, the data within receiving layer 302 may be in its raw formats. The output may then be transmitted to aggregation layer 304. In some examples, components of receiving layer 302 may have complimentary layers to facilitate data transfer. For example, the components may include a data generation and/or a data transmission layer for providing data to receiving layer 302.

Elements of aggregation layer 304 aggregate the data generated by the elements of receiving layer 302. For example, the elements of aggregation layer 304 may include aggregation engines that collect data from generation components located within receiving layer 302. Such aggregation may be performed periodically, in response to a user request, according to a schedule, or in any other suitable manner. In some examples, data of aggregation layer 304 may be aggregated according to input and/or rules and may aggregate across records pertaining to, e.g., a facility, entity, time period, characteristic (e.g., demographic characteristic or condition), outcome, and any other suitable input and/or rules. The aggregation may include compiling the data, generating a distribution, generating a statistic pertaining to the data (e.g., average, median, extremum or variance), converting the data, transforming the data to different formats, and the like.

Next, architecture stack 300 includes an active unified data layer 308. Elements of active unified data layer 308 receive data from the elements of the other layers and store such data in a unified manner. In some examples, this may include storing the data in a manner that allows for later searching and retrieval using a defined set of method calls, techniques, and or procedures. For example, the data may be stored such that a different application can access the data in a standard or unified manner. Thus, elements of active unified data layer 308 may receive information collected or generated within aggregation layer 304 and make certain adjustments to the data (e.g., translations, tagging, indexing, creation of rules for accessing the data, conversion of formatting of the data, generation of compressed versions, and the like) prior to retaining the data within one or more data stores accessible within active unified data layer 308.

Architecture stack 300 also includes an access management layer 310, which can include an audit/compliance layer 312 and/or an agency layer 314. Access management layer 310 includes elements to manage access to the data. For example, access management layer 310 may include elements to verify user login credentials, IP addresses associated with a user device, and the like prior to granting the user access to data stored within active unified data layer 308.

Audit/compliance layer 312 includes elements to audit other elements of architecture stack 300 and ensure compliance with operating procedures. For example, this may include tracking and monitoring the other elements of access management layer 310.

Agency layer 314 includes an access location (e.g., a virtual private network, a data feed, or the like) for elements of agencies that are interested in the operations of the interaction system in which architecture stack 300 is implemented. For example, agency layer 314 may allow a governmental entity access to some elements within architecture stack 300. This may be achieved by providing the governmental entity a direct conduit (perhaps by a virtual private network) to the elements of access management layer 310 and the data within active unified data layer 308. Audit/compliance layer 312 and agency layer 314 are sub-layers of access management layer 310.

Architecture stack 300 also includes interface layer 316. Interface layer 316 provides interfaces for users to interact with the other elements of architecture stack 300. For example, clients, entities, administrators, and others belonging to the interaction system may utilize one or more user devices (interacting within application/device layer 320) to access the data stored within active unified data layer 308. In some examples, the users may be unrelated to the interaction system (e.g., ordinary users, research universities, for profit and non-profit research organizations, organizations, and the like) and may use applications (not shown) to access the elements within architecture stack 300 via one or more interfaces (e.g., to access data stored within active unified data layer 308). Such applications may have been developed by the interaction system or by third-parties Finally, architecture stack 300 includes application/device layer 320. Application/device layer 320 includes user devices and applications for interacting with the other elements of architecture stack 300 via the elements of interface layer 316. For example, the applications may be web-based applications, entity portals, mobile applications, widgets, and the like for accessing the data. These applications may run on one or more user devices. The user devices may be any suitable user device as detailed herein.

Figure 4:
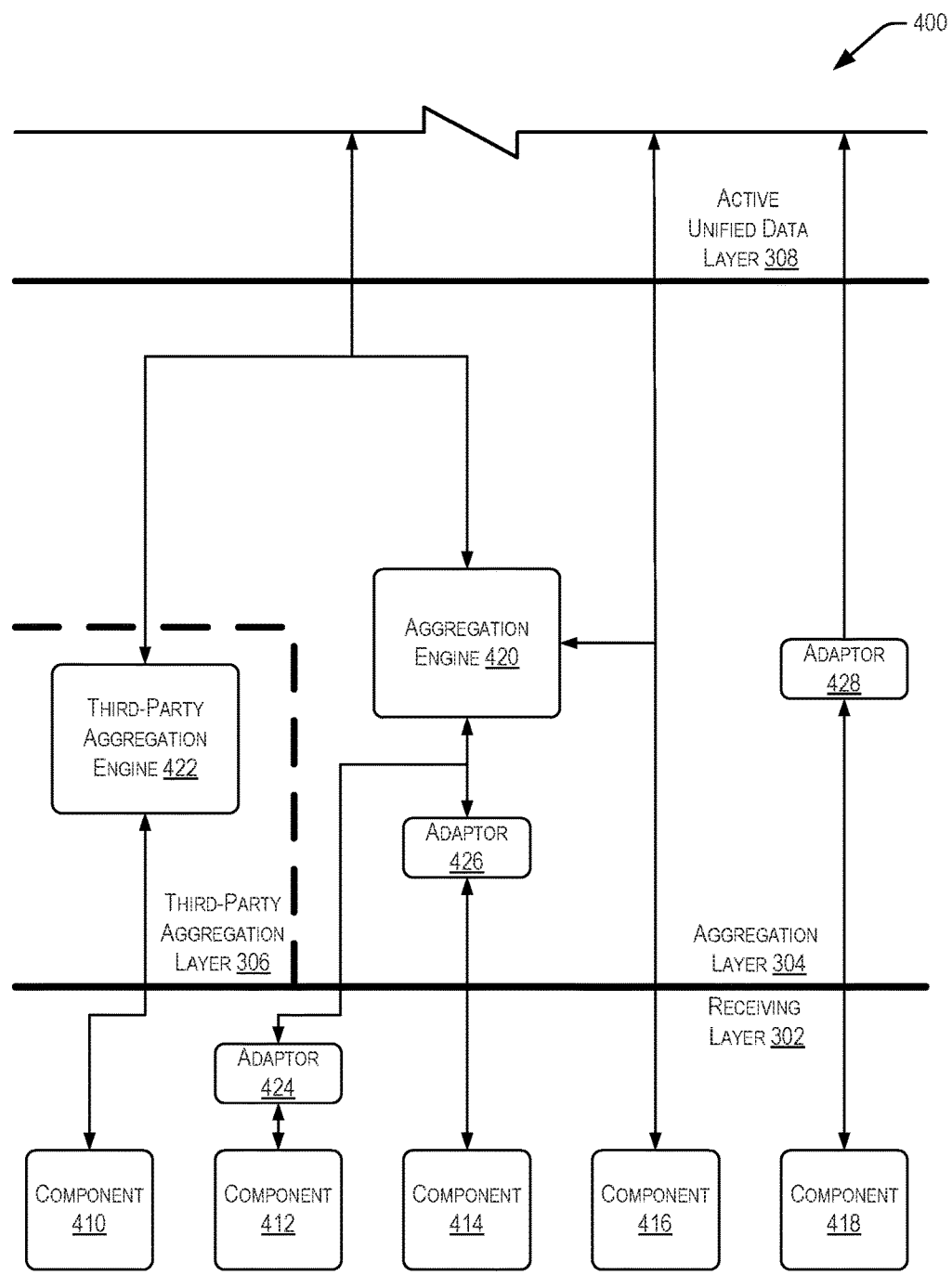
FIG. 4 shows a portion of an architecture stack according to an embodiment of the invention.

Turning next to FIG. 4, a diagram 400 is shown that depicts a portion of architecture stack 300 according to an embodiment of the invention. In particular, the diagram 400 includes receiving layer 302, aggregation layer 304, aggregation layer 306, and a portion of active unified data layer 308. Receiving layer 302 receives data from one or more components 410-418. Components 410-418 are examples of one or more generation components 204. Components 410-418 may be spread across multiple facilities within a single or multiple clients. In some examples, components 410-418 may include complimentary layers to facilitate data transmission. For example, components 410-418 may include a transmission layer, generation layer, and/or a receiving layer to communicate data at receiving layer 302 and, in some examples, receive data from receiving layer 302.

In some instances, two or more of components 410-418 generate data according to different formats. The data can then be transformed, translated, or otherwise adjusted before an aggregation engine 420 (e.g., aggregation engine 218) or a third-party aggregation engine 422 (e.g., aggregation engine 218) collects the data. In some examples, the adjustment takes place within receiving layer 302. Thus, an adaptor 424 is associated with component 412 located in receiving layer 302. Adaptor 424 is an example of transformative adaptor 216. Adaptor 424 is implemented, as appropriate, in hardware, software, or any suitable combination of both. For example, transformative adaptor 216 may be a bolt-on adaptor that adjusts data as such data leaves component 412.

Other adaptors, such as adaptor 426 and adaptor 428, are implemented within aggregation layer 304. These adaptors can function in a similar manner as adaptor 424. In some examples, the data provided by component 414 is transmitted through adaptor 426 prior to being directed to aggregation engine 420. The data provided by component 416 is transmitted through aggregation layer 304 and/or enters aggregation engine 420 without having first traveled through an adaptor. The data provided by component 418 is transmitted through aggregation layer 304 and through adaptor 428. In some examples, component 418 provides for streaming of data. The data provided by component 410 is transmitted directly to third-party aggregation engine 422.

Aggregation engine 420 and third-party aggregation engine 422 function in a similar manner. In some examples, third-party aggregation engine 422 is operated by a different entity than the entity that operates aggregation engine 420 and may belong to different clients or a different interaction system. This may be because the data collected by third-party aggregation engine 422 differs in some way from the data collected by aggregation engine 420. In any event, aggregation engine 420 is configured to perform integration of data, including generic integration. For example, aggregation engine 420 performs one or more operations on data including tagging, logging, and protocol conversion. Aggregation engine 420 also supports one-to-many communications of data. In some examples, data flows between aggregation engine 420, the third-party aggregation engine 422, and some of components 410-418 and elements of active unified data layer 308.

Figure 5:
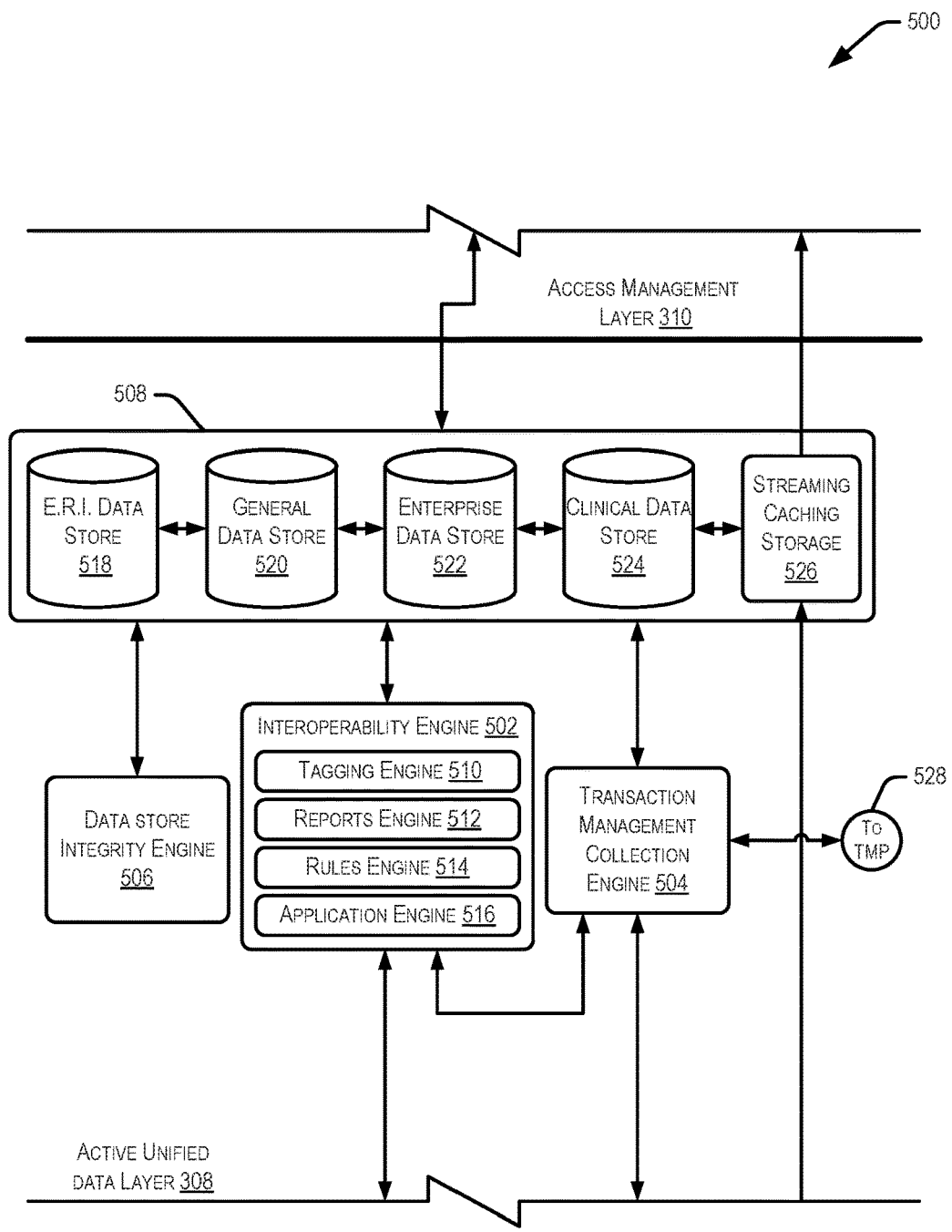
FIG. 5 shows a portion of an architecture stack according to an embodiment of the invention.

Referring next to FIG. 5, a diagram 500 is shown that depicts a portion of architecture stack 300 according to an embodiment of the invention. In particular, diagram 500 includes active unified data layer 308 and a portion of access management layer 310. Active unified data layer 308, as illustrated in diagram 500, includes an interoperability engine 502 (e.g., interoperability engine 220), a transaction management collection engine 504, a data store integrity engine 506, and a data store 508 (e.g., data store 226). Generally, interoperability engine 502 receives data from elements within aggregation layer 304 (e.g., from aggregation engine 420) and performs one or more operations with respect to the data. Interoperability engine 502 also facilitates storage of at least a portion of the processed information in data store 508.

Transaction management collection engine 504 is implemented as part of transaction management engine 106. Transaction management collection engine 504 is configured to generate message indicators identifying flows of data by and between elements of an interaction system implemented using the techniques described herein. The flows of information include messages which include data, and the message indicators include unique message identifiers that can be used to identify the messages. The unique message identifiers include information that can be used to uniquely identify the messages. For example, a unique message identifier for a particular message can include a concatenation of the following information stored in a table: a source application, a facility, a message type, and a message control identification (ID). The unique message identifier can also be the message control ID. The unique message identifier may be created as messages including data are transmitted from aggregation layer 304. The table may be stored in association with the transaction management platform 528.

In some examples, the table also includes information for tracking the progress of the message from an origination node to a destination node. For example, typically when a message (e.g., any communication of data) is first received by transformative processing engine 108 (e.g., interoperability engine 502), transaction management engine 106 (e.g., transaction management collection engine 504 of transaction management engine 106) may generate a unique identifier for the message in order to track that message as it moves throughout the interaction system. The unique identifier may be included in the header of the message such that when the next node (e.g., component, device, server, etc.) after transformative processing engine 108 receives the message, that node can report back to transaction management engine 106 that it saw the message. In this manner, transaction management engine 106 may enable end-to-end tracking of messages for the life of the message.

In one example, the messages are requests. The requests may be generated based om user input at one of the components. The requests may be received by transformative processing engine 108 and integrated into the system. In some examples, transaction management engine 106 may be notified that the requests have been received and may therefore be configured to generate message IDs for each request. These message IDs may then be associated with each of the requests. As the requests continue to move throughout the interaction system (e.g., away from transformative processing engine 108), transaction management engine 106 may be track their movement using the message IDs. If one of the requests does not make it to its destination, transaction management engine 106 (or part of the transaction management platform 528) may determine why the request was stopped. In some examples, this cause may be hardware related (e.g., an unplugged Ethernet cable, a broken router, etc.), software related (e.g., a router routing to the wrong location), or any other reason for orders not arriving at their correct destination.

In some examples, transaction management engine 106 (e.g., transaction management collection engine 504 of transaction management engine 106) may receive the message and/or message identifier directly from one of components 410-418. For example, one of components 410-416 may be configured to generate the unique message identifier and/or communicate directly with transaction management engine 106. The message also may travel via one or more intermediate nodes on its way to the destination node. In some examples, a node is a component such as components 410-418, which may be running an application. In some examples, the unique identifier and the routing of the message to its destination may be stored in a table that also includes: a geolocation of each node, a network from which the message originated, a type of node, the unique node identifier, and a time associated with the message leaving the origination node. In some examples, transaction management collection engine 504 provides unique message identifiers to other elements of the interaction system to monitor the messages as they move throughout the interaction system. Transaction management collection engine 504 also provides a portion of the unique message identifiers to a transaction management platform (indicated by a circle 528) for further analysis of the message identifiers. Such analysis may include reconciliation of lost messages, latency reporting, audit management and compliance, and other such analyses.

As mentioned previously, interoperability engine 502 is configured to store data in data store 508. A plurality of sub-engines 510-516 of interoperability engine 502 are configured to perform operations relating to storing data in data store 508.

Interoperability engine 502 includes a tagging engine 510 configured to perform semantic tagging and indexing of data. Tagging engine 510 therefore is configured to receive data, read metadata associated with the data, semantically scan the content of the data, and associate one or more tags with the data. Tagging engine 510 may therefore have access to hundreds, thousands, or even more possible tags. These tags may have been input by users, learned, pre-defined, generated by outside third-party mapping sources, and/or gathered from other components and/or data stores of the interaction system. For example, if the data is a chart for an entity, the tagging engine may be configured to read any metadata associated with the chart to determine which tags may be appropriate to associate with the chart. From the metadata, tagging engine 510 may determine that the chart is for a type of entity by reading metadata indicating that an author field is populated with the name of another particular type of entity. Tagging engine 510 may have access to other data to compare the analyzed metadata against (e.g., to identify that the author's name corresponds to Dr. Brown who is an oncologist). Other examples, of metadata that may be included in one or more fields include author, document type, creation time and date, last update time and date, upload time and data, geographic location, unique ID associated with the client or facility where the data originated, and other similar fields. The tags may be stored in association with the data (e.g., the chart) and/or may be stored independent from the data but include an identifier such that when searching tags the data may be capable of population.

Continuing with the example from above, if the data is a chart for a first type of entity, tagging engine 510 may be configured to read the content of the chart to determine which tags may be appropriate to associate with the chart. For example, this may comprise analyzing the content of the chart (i.e., individual pages) semantically to look for artifacts (e.g., keywords, phrases, and the like) in the content. These artifacts may be identified by tagging engine 510 and used to decide which tags to associate with the document. In some examples, semantic scanning may involve filtering out words (e.g., articles, such as "a" and "the"), phrases, and the like. Similar to the reading of metadata, the tags may be pre-defined, user-defined, learned, and the like. In some examples, reading metadata associated with messages may provide meaning and/or give context to the particular record of data. This meaning and/or context may assist tagging engine 510 to determine one or more tags to associate with the data. The tags may be chosen, for example, based on values of particular fields in the data, detecting a frequency of one or more words in a document or metadata and/or of a set of related words (e.g., tagging a record with "cancer" upon detecting words such as tumor, metastasize, chemotherapy, radiation, oncology, malignant, stage 3, etc.). In this manner, tagging engine 510 may also index portions of the data within one or more data stores of data store 508. In some examples, such indexing may be based in part on the selected tags.

Interoperability engine 502 also includes a reports engine 512 configured to generate one or more reports or alerts based on data. For example, reports engine 512 may generate reports when certain types of data are received or when data with certain characteristics is received. Reports engine 512 may also generate alerts. The reports and/or alerts generated by reports engine 512 may be outputted in the form of one or more communications to an administrator, an authorized user, or other similar user via a user device. Such communications can include, for example, signals, sirens, electronic notifications, popups, emails, and the like. Content of such communications may include information characterizing a performance metric, efficiency and/or outcomes; identifying concerning patterns; identifying losses of data; and the like. In some examples, the content is presented in the form of one or more documents, tables, figures, charts, graphs, and the like.

Interoperability engine 502 also includes a rules engine 514 configured to create and manage business rules, condition-response rules, alert/reports rules, data-formatting rules, data-sharing rules, transmission rules, aggregation rules, user authorization rules, and other similar rules. Such rules may be user-defined, fixed, learned by elements of the interaction system, and any combination of the foregoing. Finally, interoperability engine 502 includes an application engine 516 configured to provide service-oriented architecture web services.

Data store 508 includes an electronic record information data store 518 ("record data store 518"), a general data store 520, an operational data store 522, an entity-based data store 524, and a streaming caching storage 526. While data store 508 is illustrated as including a fixed number of data stores and storage elements, it is understood that data store 508 can include any suitable number of data stores and storage elements, including more than illustrated or less than illustrated.

In some examples, a data query script is provided to query a first data store and/or to obtain data for populating a data store. Such script could query a data store described herein (e.g., data store 508) and/or could be used to obtain data to populate a data store described herein (e.g., data store 508). In one instance, the script is configured to be repeatedly executed, so as to repeatedly draw data from a source data store. The retrieved data can then be formatted, filtered, sorted and/or processed and then stored, presented and/or otherwise used. In this manner, the script can be used to produce streaming analytics.

In some instances, the data query script, when executed, identifies each of the data stores of interest. Identifying the data stores of interest involves identifying at least a portion of data from the data stores simultaneously and/or sequentially. For example, the script can identify corresponding data stores (e.g., or components of a single data store or multiple data stores) that pertain to one or more similar variables but that differ in one or more other variables. Once the portion of the data from the data stores is identified, a representation of the identified data can be output to one or more files (e.g., Extensible Markup Language (XML) files) and/or in one or more formats. Such outputs can then be used to access the data within one or more relational database accessible using Structured Query Language (SQL). Queries made using SQL can be made sequentially or in parallel. Results from an SQL query may be stored in a separate database or in an XML file that may be updated either in part or as a whole. The data query script may be executed periodically, in accordance with a user-defined rule, in accordance with a machine-defined or machine-learned rule, and in other suitable manner.

[Within record data store 518 is retained data including electronic record information. In some examples, the information within record data store 518 is organized according to entity identifying information. Thus, record data store 518, in some examples, includes individually identifiable information. But it may also include de-identified information.

Within general data store 520 is retained data. The data may be stored in a relational database format or in any other suitable format. Thus, the data within general data store 520 may be retained in a data structure that includes one or more tables capable of accessing each other. In some examples, general data store 520 includes a subset of the information that is included in operational data store 522.

Within operational data store 522 is retained data in a relational database format. Thus, the data within operational data store 522 may be retained in a data structure that includes one or more data structures (e.g., tables) capable of accessing each other. Operational data store 522 is an example of an operational data warehouse. In operational data store 522 is joined many different types of data. F2. In some examples, the operational data ware house 522 includes data pertaining to decision making as discussed herein and other data typically used by conventional business concerns.

Within entity-based data store 524 is retained data in a non-relational database format. Thus, the data within entity-based data store 524 may be retained in a structure other than tables. Such structure may be appropriate for large and complex data sets. In some examples, entity-based data store 524 (or any other data store) may be a unified system, which may include: a document-centric, schema-agnostic, structure-aware, clustered, transactional, secure, database server with built-in search and a full suite of application services. An example of such a unified system may be Marklogic. Entity-based data store 524 can support data aggregation, data organization, data indexing, data tagging and mapping to semantic standards, concept matching, concept extraction, machine learning algorithms, concept discovery, concept mining, and transformation of personal record information. In some examples, entity-based data store 524 includes data pertaining to decision making (similar to general data store 520) as discussed that is organized and accessed in a different manner. For example, the data within entity-based data store 524 may be optimized for providing and receiving information over one or more information exchanges. In some examples, entity-based data store 524 includes a subset of the information that is included in operational data store 522.

Finally, in some examples, streaming caching storage 526 is a streaming data cache data store. As discussed previously, certain components of components 410-418 may support streaming data to other components or user devices. Streaming caching storage 526 is a location where streaming data can be cached. For example, assume that component 418 is a piece of equipment operating at Location A and that a user using a computer in Location B desires to view a live of substantially live stream of outputs of the piece of equipment. Component 418 can send a portion of data to streaming caching storage 526 which can retain the portion of the data for a certain period of time (e.g., 1 day). Thus, streaming caching storage 526 is configured to cache data that can be streamed.

Diagram 500 also includes data store integrity engine 506. In some examples, data store integrity engine 506 is configured to ensure integrity of the information within data store 508. For example, data store integrity engine 506 applies one or more rules to decide whether information within all or part of data store 508 should be scrubbed, removed, or adjusted. In this manner, confidence is increased that the information within data store 508 is accurate and current.

Figure 6:
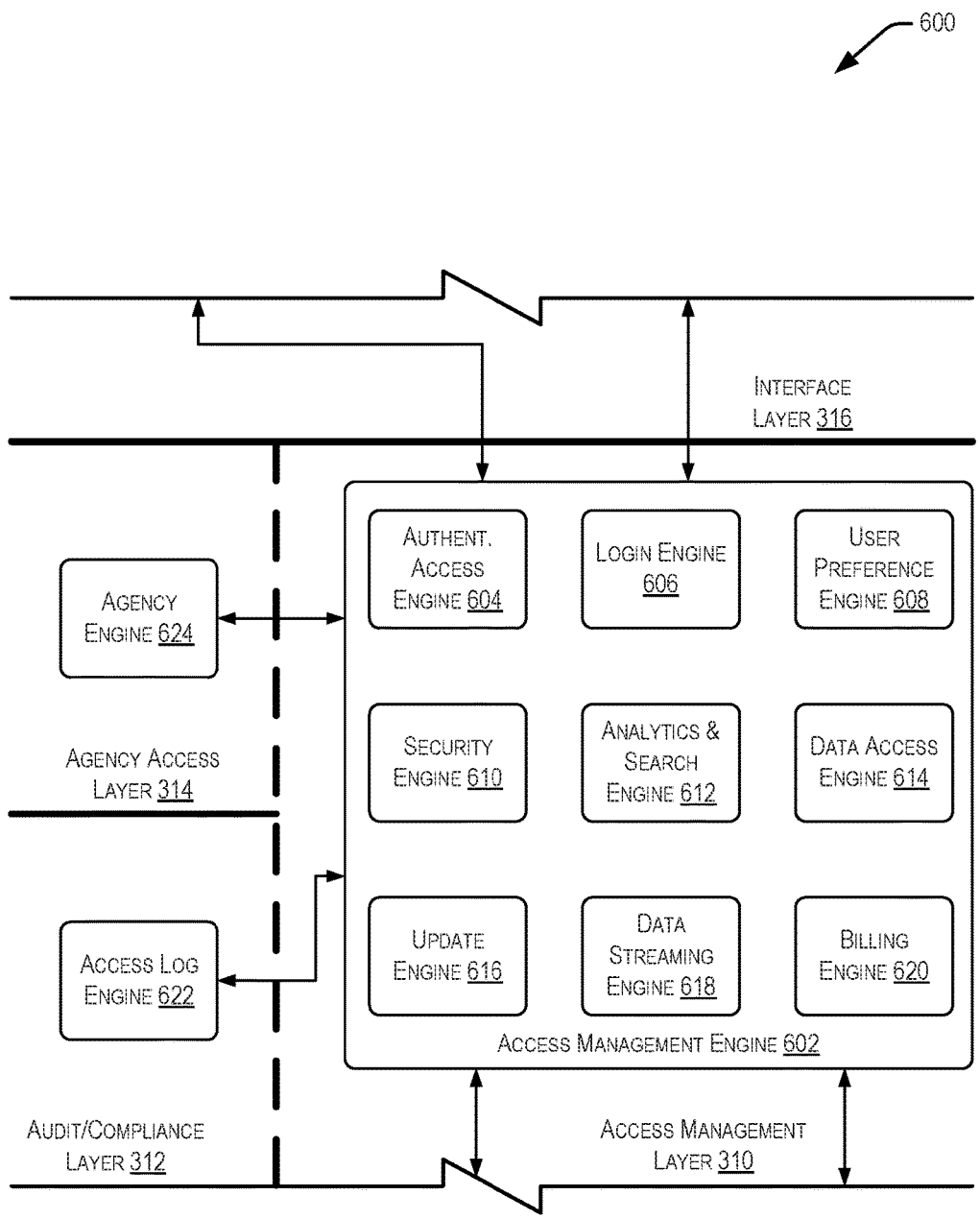
FIG. 6 shows a portion of an architecture stack according to an embodiment of the invention.

FIG. 6 shows a diagram 600 which depicts a portion of architecture stack 300 according to an embodiment of the invention. In particular, the diagram 600 includes access management layer 310, audit/compliance layer 312, agency layer 314, and a portion of interface layer 316.

Access management layer 310, as illustrated in the diagram 600, includes an access management engine 602. Access management engine 602 is an example of access management engine 222. Generally, access management engine 602 can be configured to manage access to elements of transformative integration engine 202 by different components, applications, and user devices.

Access management engine 602 within access management layer 310 also provides functionality similar to an operating system. For example, access management engine 602 includes a plurality of engines configured to manage different aspects of interacting with elements of the interaction system. For example, a user who desires to access portions of data retained in data store 508, may do so by interacting with access management engine 602 using one or more applications (not shown). Thus, access management engine 602 includes a variety of engines to enable such interaction. The engines include, for example, an authentication access engine 604, a login engine 606, a user preference engine 608, a security engine 610, an analytics and search engine 612, a data access engine 614, an update engine 616, and a streaming data engine 618. The different engines of access management engine 602 can define routines, protocols, standards, and the like for interacting with elements of the interaction system.

Beginning first with authentication access engine 604, authentication access engine 604 evaluates the rules and conditions under which users may access elements of the interaction system; in particular, the conditions under which users may access data within data store 508. These rules and conditions may be user-defined (e.g., by an administrator or reviewer), learned over time, and/or may be dynamically updated and/or evaluated based on characteristics of the user or the user's device attempting to access the interaction system. The rules and conditions may indicate the types of users who have particular types of access within the interaction system. The type of access may also relate to the degree to which data is identified/de-identified. In some examples, a user desiring access to data provides certain identifying information and authentication access engine 604 authenticates an identity of the user.

Login engine 606 evaluates the rules and conditions under which users are able to log in to the interaction system or access applications associated with the interaction system. These rules and conditions may be user-defined (e.g., by an administrator), learned over time, and also may be dynamically updated and/or evaluated based on characteristics of the user or the user's device attempting to access the interaction system. Thus, while authentication access engine 604 evaluates the rules to determine which users may access the interaction system, login engine 606 evaluates the particular credentials, profiles, etc. of the users. For example, login engine 606 can confirm that an entered username (e.g., and password), provided biometric data or code or identifier in a scanned tag or badge matches that in an authorized user data structure.

Login engine 606 evaluates one or more user profiles associated with each authenticated user. In some examples, a user profile includes a username, password, and other information associated with the user. For example, a user profile may indicate characteristics about the user.

User preference engine 608 evaluates the rules and conditions under which user are able to store and update one or more user preferences corresponding to access of the interaction system or access to applications associated with the interaction system. These rules and conditions may be user-defined (e.g., by the user or administrator), and may include rules for default preferences. For example, using user preference engine 608, a user may indicate a format in which the user prefers to receive outputted information, display characteristics of a graphical user interface associated with the user, and other similar user preference settings. For example, the user may indicate that certain types of reports and/or alerts are to be sent to the user.

Security engine 610 evaluates the rules and conditions for ensuring the security of access to the elements of the interaction system. In some examples, these rules and conditions are determined by administrators of the interaction system. In some examples, security engine 610 provides a plurality of computer virus protection services. These services can be called up and implemented when accessing the interaction system or accessing applications associated with the interaction system. The rules and conditions may be based on roles, based on profiles, based on domains, and any other suitable security configuration. For example, because the interaction system may include sensitive data, security engine 610 may enforce a domain-based rule that protects certain sensitive information (e.g., identifying information).

Analytics and search engine 612 evaluates the rules and conditions under which users can search for data within the interaction system and access analytics relating to the interaction system. In some examples, these rules and conditions are user-defined or learned over time in accordance with search engine optimization techniques. For example, analytics and search engine 612 is used to search within data store 508 for particular data. Analytics and search engine 612 supports any conventional searching algorithms. For example, search engine 612 can be used to search within various fields and potential field values. In some examples, search engine 612 can provide analytics, such as statistics, graphs, distributions and/or comparative analysis pertaining to particular entities and/or characteristics. Such information may be selected by a user and presented on a user interface.

Data access engine 614 evaluates the rules and conditions under which users may operation in order to access particular data within data store 508. In some examples, these rules and conditions are user-defined or learned over time. For example, data access engine 614 may indicate the routines, subroutines, or other logic needed for an application to access certain portions of data store 508. For example, while authentication access engine 604 and login engine 606 may manage which users can access parts of the interaction system, data access engine 614 may manage how authenticated users access data within data store 508. To this end, data access engine 614 may enforce and/or evaluate certain rules managing how users access different components of the interaction system. In some examples, data access engine 614 may be used to actually access data within data store 508 (e.g., extract, download, or otherwise access). In some examples, data access engine 614 may define procedures, protocols, and the like for accessing data. The protocols and procedures for accessing data access engine 614 (like the other engines of access management engine 602) may be provided to developers in the form of a software development kit (SDK). SDKs may enable developers write applications that can effectively communicate with elements (e.g., data store 508) of the interaction system. In particular, applications that can access a portion of the data stored within active unified data layer 308.

Update engine 616 evaluates the rules and conditions for providing updates to other engines within access management engine 602, plug-ins for applications that access the interaction system, and for other similar elements of the interaction system. For example, updates may be generated at runtimes, at defined time intervals, upon request by a user, upon receiving a threshold quantity of new or changed data. Once an update is performed, an interface may be refreshed, a report may be sent indicating that the update was successful or unsuccessful, or the like.

Streaming data engine 618 defines the rules and conditions for enabling streaming of data between components and user devices of the interaction system. For example, streaming data engine 618 may enable component 414 to stream data. Streamed data may include live or substantially live audio or video feeds, results of tests, output from equipment or devices, and any other suitable type of data capable of being streamed. In some examples, the data may be streamed to other components or user devices within the network or outside the network. In order to establish a streaming transmission, streaming data engine 618 may identify a streaming destination and a streaming origin. Next, streaming data engine 618 may pair the two and enable streaming. This may include allocated bandwidth within one or more network devices associated with the interaction system. Streaming data engine 618 may also adjust the quality of the streaming data based on the availability of bandwidth. In some examples, streaming data engine 618 may receive incoming streams (and continuously present the stream or monitor for particular data (e.g., exceeding a threshold, exhibiting an above-threshold change, having a particular value)).

Within audit/compliance layer 312 is located an access log engine 622. Access log engine 622 evaluates the rules and conditions for logging access to the interaction system by users, applications, devices, and the like. Logging access includes, in some examples, logging data conventionally collected by access log engines running in similar environments. Access log engine 622 can use this data to generate and transmit reports, for example, to stakeholders of the interaction system such that they can make informed decisions regarding that is accessing the interaction system and for what purposes.

Within agency layer 314 is located an agency engine 624. Agency engine 624 evaluates the rules and conditions under which agencies can access the interaction system. For example, agencies that may use agency engine 624 include agencies to which the interaction system provides compliance, tracking, or other reporting information. For example, agency engine 624 may be used to track one or more performance indicators identified by a government agency and/or to provide report instances of defined types of events. Thus, in some examples, a government agency uses agency engine 624 to collect data pertaining to compliance of the interaction system with one or more statutes or regulations. In some examples, a university is an agency that uses agency engine 624 to collect data pertaining to one or more studies. In some examples, agency engine 624 can identify one or more entities (e.g., governmental agencies) that are to receive reports pertaining to operations or events and what types of data are to be reported to those entities. Agency engine 624 can then collect the pertinent data, potentially format and/or analyze the data, and facilitate transmission of (e.g., raw, formatted and/or analysis of) the data to the appropriate agency.

Figure 7:
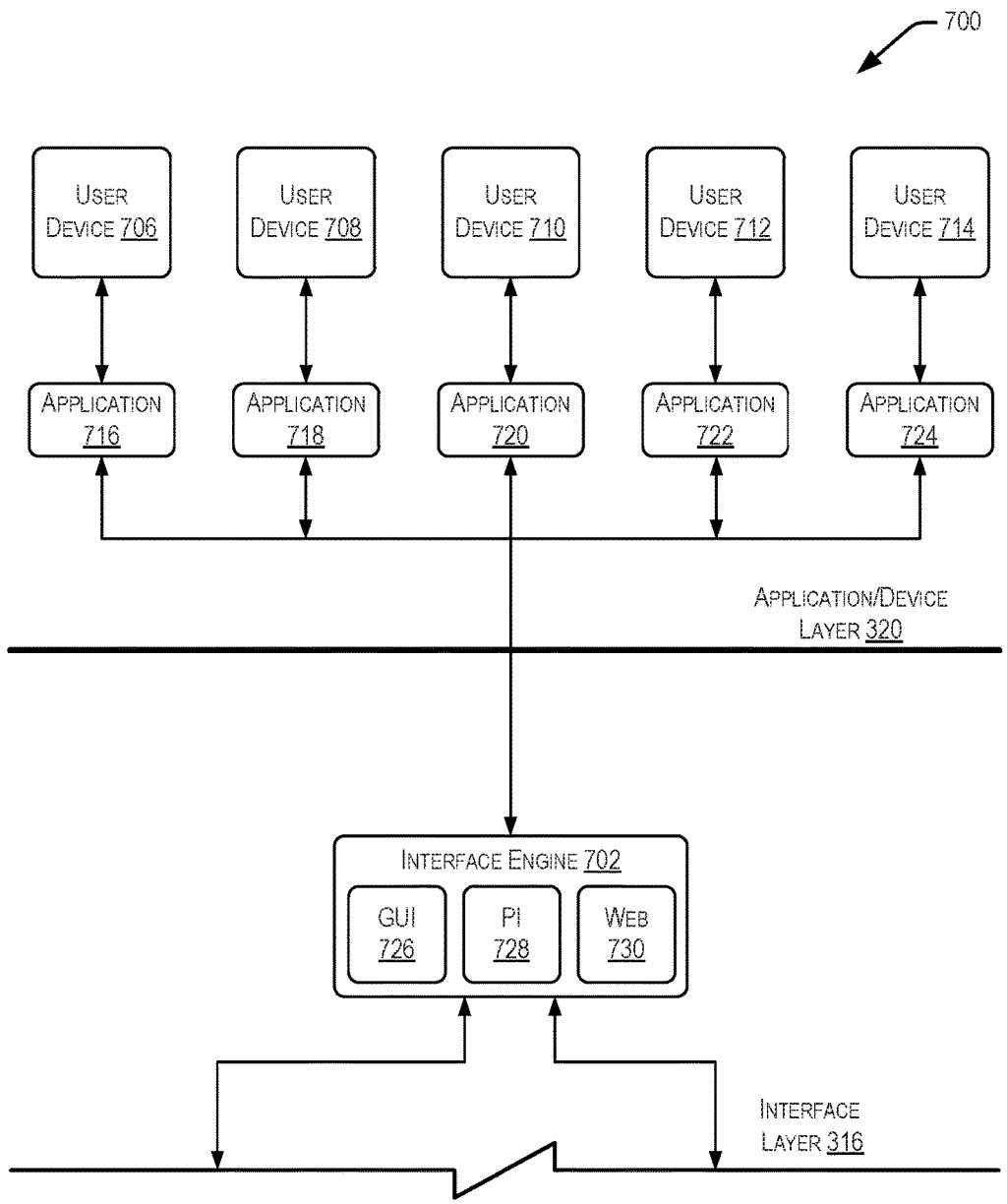
FIG. 7 shows a portion of an architecture stack according to an embodiment of the invention.

FIG. 7 shows a diagram 700 which depicts a portion of architecture stack 300 according to an embodiment of the invention. In particular, diagram 700 includes interface layer 316, and application/device layer 320. Within interface layer 316 is located interface engine 702 (e.g., interface engine 224). Interface engine 702 is configured to generate one or more interfaces (e.g., graphical user interface 726, programmatic interface 728, and/or web interface 730) to enable data to flow to user devices 710, 712, and 714 via respective applications 720, 722, and 724. In some examples, the interfaces of interface engine 702 are embodied in hardware, software, or some combination of both. Within interface layer 316 communications and inputs directed to interacting with elements of access management layer 310 may be embodied.

Graphical user interface 726 is any suitable graphical user interface configured to interact with elements of the interaction system. Programmatic interface 728 includes an application programming interface, a programmatic user interface, and other similar interfaces for defining core functions for accessing elements of the interaction system. For example, programmatic interface 728 may specify software components in terms of their operations. Web interface 730 is any suitable web interface configured to interact with elements of the interaction system. Any of the interfaces described herein may be configured to receive user input, present dynamic presentations that depend on user input, and otherwise respond to user input. In some examples, such input may be provided via one or more input devices (e.g., a keyboard, touchscreen, joystick, mouse, microphone, devices capable of capturing inputs, and the like) operated by one or more users of user devices 706-714. Output may be provided via one or more output devices (e.g., a display or speaker).

Interface engine 702 is utilized by applications internal to the interaction system and external to the interaction system to access data. In some examples, the applications that are internal include applications that are developed for internal use by various entities associated with the interaction system. In some examples, the applications that are external to the interaction system include applications that are developed for external use by those that are not associated with the interaction system.

Generally, within application/device layer 320, applications 716-724 which communicate with other elements of architecture stack 300 using the interfaces generated by interface engine 702 are defined. This includes detailing how applications 716-724 are to interact with the interfaces generated by interface engine 702 for accessing data. For example, interacting may include accepting inputs at user devices 706-714 to access data and, in response, providing the data, prompts, or other types of interaction with one or more users of the user devices 716-714. Thus, applications 716-724 may be related to one or more of the interfaces generated by interface engine 702. For example, application 720 may be interact with a graphical user interface (whether generated by interface engine 702 or otherwise) to interact with other elements of the interaction system. Interacting may include receiving inputs at the graphical user interface via application 720, providing output data to the graphical user interface application 720, enabling interaction with other user devices, other applications, and other elements of the interaction system, and the like. For example, some of the inputs may pertain to aggregation of data. These inputs may include, for example, types of data to aggregate, aggregation parameters, filters of interested data, keywords of interested data, selections of particular data, inputs relating to presentation of the data on the graphical user interface, and the like. Providing output data may include providing the aggregated data on the graphical user interface, outputting the information to one of the other user devices 706-714 running one of the other applications 716-724.

Turning now to the details of applications 720, 722, and 724. In some examples, applications 720, 722, and 724 include a variety of different applications that can be designed for particular users and/or uses. In one example, application 720 includes dashboards, widgets, windows, icons, and the like that are customized for an particular entity. In some examples, application 720 may present different data depending on a specialty associated with the entity and protected information associated with the entity. In this manner, application 720 adapts and automatically adjusts depending on the context in which the entity is using the application. In some examples, the data indicates performance statistics for the entity, metrics relating to where the entity falls along a distribution of other similar entities, outlier instances, trends in events or actions, and the like. Application 720 may be configured to receive input, adjust presentations, present unprompted alerts, adjust display of content, move more relevant content to the foreground, move less relevant content to the background, populate forms for the entity.

In another example, application 722 may be specific for nurses or types of nurses. In this example, application 722 may include dashboards, widgets, windows, icons, and the like that are customized to individual nurses. Similar to the example discussed above pertaining to the doctor, in some examples, application 724 may present different data depending on a position of the nurse. In this manner, application 722 adapts and automatically adjusts depending on the context in which the nurse is using the application. For example, the nurse may receive data, such as test results.

In some examples, application 724 may be a multi-role application for administrators and is used to manage entities constitute the population of the entities or organizations within the interaction system. Similar to the other examples discussed, in some examples, application 724 may present different data depending on a role of the user who is using application 724. In this manner, application 724 adapts and automatically adjusts depending on characteristics of the user who is using application 724. In this manner, application 724 can provide different data depending on the role of the user. For example, whether data presented includes identifiable or de-identified information may depend on a position of the user.

In some examples, application 724 may be a business intelligence application. In this example, application 724 is used to display business information generated by components of the interaction system. This business information can be used for operations, planning, and forecasting. Such business information may include data because such data may impact operations, planning, forecasting, and the like. Accordingly, application 724 may present de-identified information in the form of one or more metrics, indicators, or the like as they pertain to business intelligence.

Applications 716 and 718 shown in connection with interface engine 702 are applications developed by third-parties. In some examples, such applications include any suitable application that benefits from accessing data. The interaction system may include data pertaining to hundreds of thousands of entities. Having data pertaining to so many entities presents security concerns. For example, much of the data may be identifying data. Accordingly, data that may be accessed by applications 716 and 718 may be limited. In some examples, an entity of the interaction system may use one of applications 716, 718 to access his or her own data.

In this example, the identity of the entity may be verified in accordance with techniques described herein.

User devices 706-714 are any suitable user devices capable of running applications 716-724. User devices 706-714 are examples of the user device 228. In some examples, the user devices include: mobile phones, tablet computers, laptop computers, wearable mobile devices, desktop computers, set-top boxes, pagers, and other similar user devices. In some examples, at least some of user devices 706-714 are the same devices as at least some of the one or more components 410-418. In some examples, user devices 706-714 may include complementary layers to application/device layer 320 and/or receiving layer 302. For example, user devices 706-714 may include a transmission layer, a generation layer, and/or a receiving layer to communicate data at application/device layer 320 and at receiving layer 302.

Figure 8:
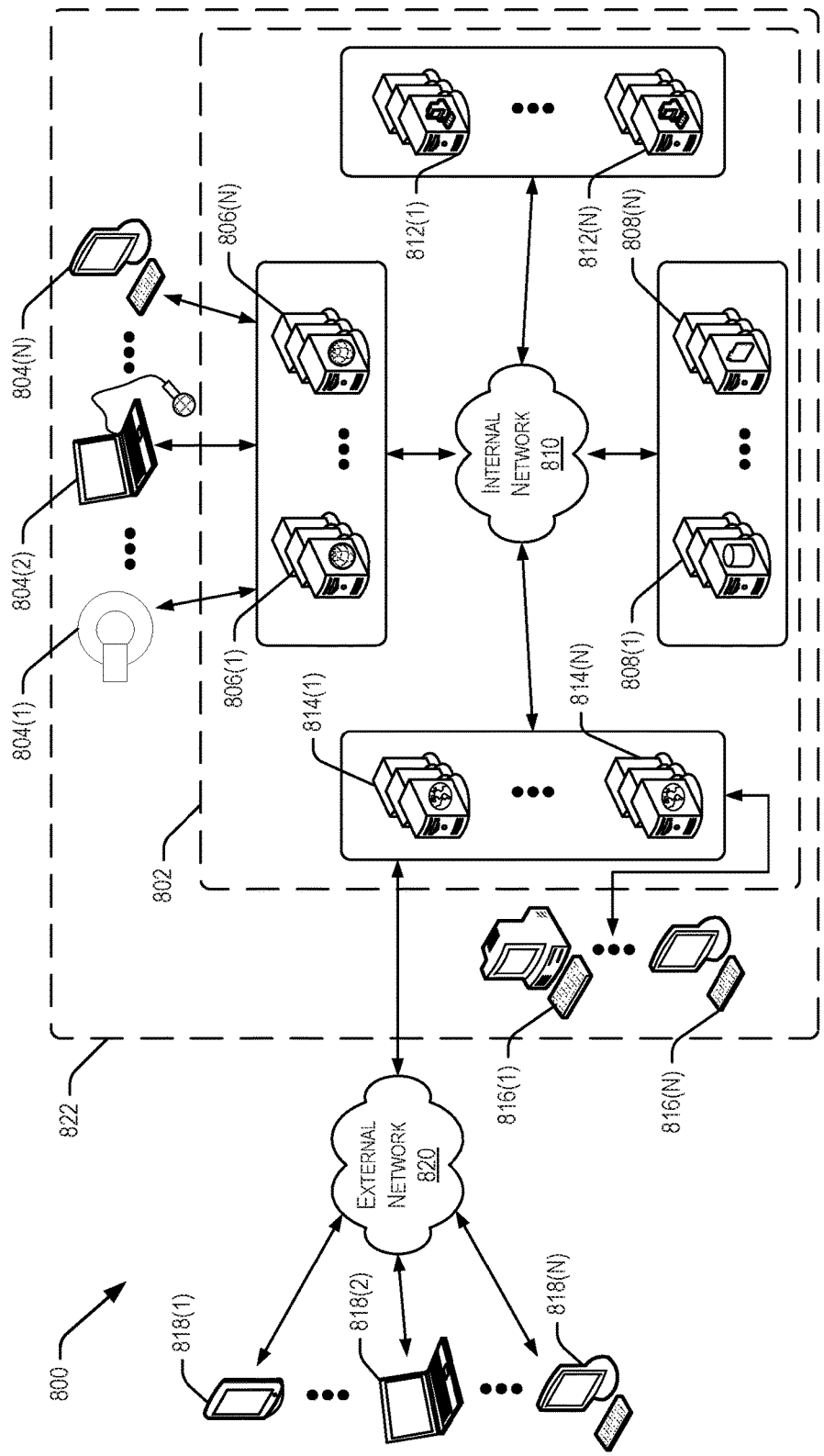
FIG. 8 shows an interaction system in accordance with an embodiment of the invention.

Turning now to FIG. 8, an interaction system 800 is shown in accordance with an embodiment of the invention. Interaction system 800 includes an internal organization 822 including a transformative integration engine 802. The transformative integration engine 802 is an example of transformative integration engine 202 previously discussed. Interaction system 800 is illustrated as an example configuration for implementing the techniques described herein. In particular, a configuration of elements as illustrated in FIG. 8, at least in some examples, communicates according to the layers of architecture stack 300. For example, internal organization 822 includes generation components 804(1), 804(2), and 804(N) which provide data to aggregation servers 806(1)-806(N).

Generation components 804(1), 804(2), and 804(N) operate in accordance with receiving layer 302. In some examples, generation component 804(1) is a piece of equipment, generation component 804(2) is computer with a data collection device, a type of lab system, and generation component 804(N) is a terminal. Aggregation servers 806(1)-806(N) operate in accordance with aggregation layer 304. Aggregation servers 806(1)-806(N) share data with data storage servers 808(1)-808(N) via one or more internal network(s) 810. In some examples, internal network 810 is any suitable network capable of handling transmission of data. For example, internal network 810 may be any suitable combination of wired or wireless networks. In some examples, internal network 810 may include one or more secure networks. Data storage servers 808(1)-808(N) are configured to store data in accordance with active unified data layer 308. Data storage servers 808(1)-808(N) include database servers, file storage servers, and other similar data storage servers.

Access management servers 812(1)-812(N) manage access to the data retained in the data storage servers 808(1)-808(N). Access management servers 812(1)-812(N) communicate with the other elements of interaction system 800 via internal network 810 and in accordance with access management layer 310.

Interface servers 814(1)-814(N) provide one or more interfaces applications to interact with the other elements of interaction system 800. Interface servers 814(1)-814(N) provide the one or more interfaces and communicate with the other elements of interaction system 800 via internal network 810 and in accordance with interface layer 316. The interfaces generated by the interface servers 814(1)-814(N) can be used by internal user devices 816(1)-816(N) and external user devices 818(1), 818(2), and 818(N) to interact with elements of interaction system 800.

Internal user devices 816(1)-816(N) are examples of user devices 706-714. In some examples, internal user devices 816(1)-816(N) run applications via the interfaces generated by interface servers 814(1)-814(N). As an additional example, external user devices 818(1), 818(2), and 818(N) can run applications developed by third parties that access the other elements of interaction system 800 via the interfaces generated by interface servers 814(1)-814(N).

External user devices 818(1), 818(2), and 818(N) access the interfaces via external network 820. In some examples, external network 820 is an unsecured network such as the Internet. External user devices 818(1), 818(2), and 818(N) are examples of user devices 706-714. External user device 818(1) is a mobile device. In some examples, the mobile device may be configured to run an application to access interaction system 800. Similarly, the other external user devices 818(2)-818(N) run applications that enable them to access interaction system 800. While interaction system 800 is shown as implemented using discrete servers, it is understood that it may be implemented using virtual computing resources and/or in a web-based environment.

Figure 9:
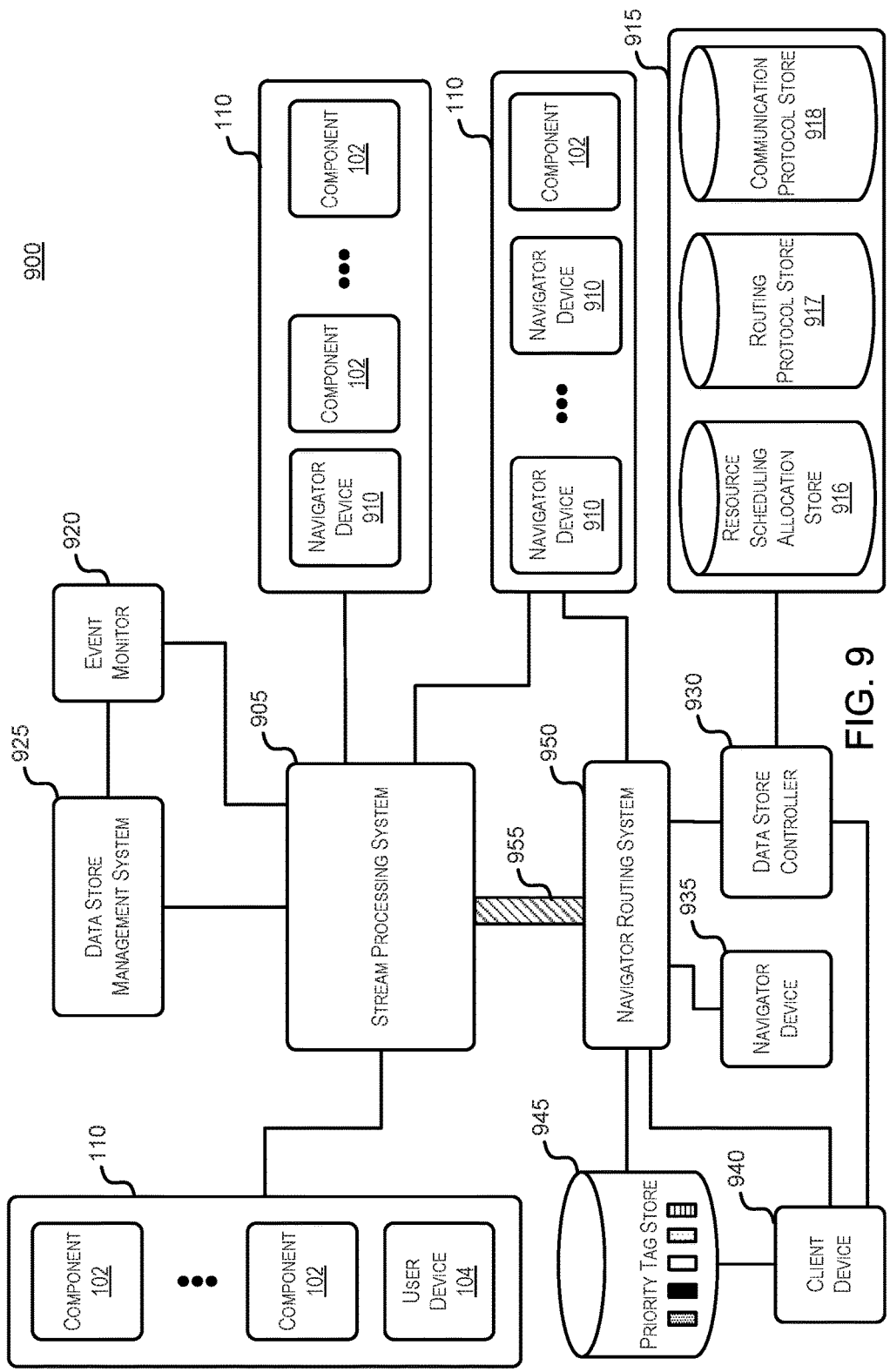
FIG. 9 shows a block diagram of another embodiment of an interaction system.

FIG. 9 shows a block diagram of another embodiment of an interaction system. Interaction system 900 may include a stream processing system 905, facilities 110, data stores 915, event monitor 920, data store management system 925, data store controller 930, client device 940, priority tag store 945, and navigator routing system 950.

Navigator devices 910 may include devices associated with a navigator. A navigator may correspond to a resource (e.g., a physician, a nurse, a medical assistant, etc.). Examples of one or more navigator devices 910 can include, for example, a computer, a mobile device, a smart phone, a laptop, an electronic badge, a set-top box, a thin client device, a tablet, a pager, and other similar navigator devices. One or more navigator devices 910 may be configured to run one or more applications developed for interacting with data collected by transformative processing engine 108. For example, those navigator devices of the one or more navigator devices 910 that are not associated with facility 110 (e.g., navigator device 935) may be configured to run one or more third-party applications that may rely in part on the data gathered by transformative processing engine 108.

Generally, in interaction system 900, data can be generated at one or more system components 102, user devices 104, and/or navigator devices 910. Data from various components 102, user devices 104, and/or navigator devices 910 can be included in one or more data streams (e.g., as source data) transmitted to stream processing system 905.

In some instances, data collected (e.g., via sensors or user interface components) at a component 102 and/or user device 104 can immediately, or with some delay (e.g., so as to be at an end of a data-collection effort) appended to a data stream transmitted directly or indirectly to stream processing system 905. In some instances, collected data can be locally or remotely stored and subsequently retrieved (e.g., by a same or different device) to append to a stream. For example, a set of components 102 and/or user devices 104 may collect and/or generate data and then store the data. A managing server may then, at a defined time or upon detecting a defined type of event (e.g., receiving a data request or detecting a threshold size of a data stream), retrieve the stored data and append the data (e.g., in raw or processed form) to a stream. Thus, a source of a stream may be a single component or user device or an intermediate device or system that collects data from multiple components and/or user devices.

Data included in streams may include data collected (e.g., via sensors or an input interface that detects, for example, verbal, typed or cursor inputs) and/or other data. For example, other data may include information and/or an identifier of a facility, a navigator device, a navigator associated with a navigator device, a time, a location, a title of an agent having initiated a data collection, a workflow or decision tree associated with the data collected, and so on. As another example, other data may include information retrieved from a stored object that is related to collected data. To illustrate, data collected via a component may include data detected by a sensor that is receiving biological signals from a given person, and the other data may include characteristics pertaining to the person or a workflow for a resource associated with the data detected by the sensor.

A data stream may include a plurality of data elements in succession. Each data element in a stream may be assigned an index. Indices may be used to monitor whether and/or an extent to which data elements are being reliably transmitted and received at a destination. The indices may correspond to an order in which data elements are appended to the stream. Thus, monitoring a stream-transmission reliability may then include detecting whether data elements corresponding to each of a set of sequential indices have been received at a destination.

Stream processing system 905 can be configured to receive, transform, route and/or store data elements from each of one or more streams. Further, stream processing system 905 can also be configured to receive, transform, route and/or store one or more data streams included or contained within a received stream. Stream processing system 905 can include, for example, a transaction management engine (e.g., transaction management engine 106) and/or transformative processing engine (e.g., transformative processing engine 108).

Stream processing system 905 may, in some instances, be remote from one, more or all sources of data streams being processed. Stream processing system 905 may include one or more servers (e.g., a server farm) that may include a collection of specialized stream processing engines (e.g., each engine being a server or processing core). A stream processing engine may be specialized so as to include, for example, fast multi-lean memory buses (e.g., a 128-bit or 256-bit wide interconnections). A stream processing engine may be configured for bulk memory transfers. For example, a Stream Register File (SRF) can store stream data to be transferred to external data stores in bulks and specialized chips (e.g., the Imagine chip) can facilitate strategic flow and packing of the SRFs.

Various processors and/or layers within stream processing system 905 can be specialized to perform various types of tasks. For example, a first set of processors may be configured to transform data within the stream in real-time (e.g., to produce data in a standard format and/or one that corresponds to a communication protocol) and detect (e.g., based on data included in a header of a data element) whether the transformed data includes one or more particular composites (e.g., or fields). The first set of processors may thus be configured to perform on-chip processes with low latencies.

Upon detection of such one or more particular composites within a data element, a first processor may transmit the data element (or a replicated version thereof) to one or more second processors, which may be configured to perform more specialized extraction, apply a processing of a rule, request and/or retrieve data from a remote data source, and/or store data associated with the data element (e.g., in a L1, L2, or L3 Cache, a local RAM or a remote data store).

One or more third processors may be configured to securely communicate with one or more event monitor devices 920 (e.g., which may be associated with a particular facility and/or an agency having authority over a given facility or population). Such communications may include, for example, receiving and/or responding to a request for one or more report communications and/or transmitting one or more report communications. Event monitor devices 920 to which reports are transmitted may include devices identified via a report protocol (e.g., such that a report protocol includes an identification of a particular event monitor device; an identification of a facility or agency associated with an event monitor device; or an identification of a webpage or website associated with the particular event monitor device). A report can include, for example, data from and/or identifications of data elements flagged during a report-protocol performance (or processed version thereof); an identification of one or more data sources; a count (e.g., of flagged data elements) and/or an index or storage address associated with each of one or more of the flagged data elements. The report may include data in a format corresponding to that required or otherwise associated with a corresponding event monitor. Thus, in some instances, the one or more third processors may transform the data (e.g., from a standard format to an event-monitor format). A report communication can be transmitted to an event monitor 125, e.g., via file upload (e.g., SFTP, SSH, FTP), web interaction, email, etc., and the type of communication may include one specified in a corresponding report protocol.

It will be appreciated that, in various instances, one or more of the depicted devices may be co-located. As mere illustrations, a protocol generator device 124 may be located in a same geographic area (e.g., building, city, zip code, district or state) as one or more data-collection devices (e.g., component 102 or user device 104).

Some or all of the data in streams being processed by stream processing system 905 may be routed to one or more data store management systems 925, which can store the data at one or more non-volatile memory stores and/or respond to requests (e.g., from an event monitor device 920) to retrieve specific data. For example, data store management system 925 may maintain a data structure that relates one or more indices to a storage location or address. An index may uniquely relate to, for example, a data element, composite, subject, source, facility and so on. Thus, it will be appreciated that, in some instances, a storage address can correspond to a plurality of indices, and—depending on a type of an index—a plurality or storage addresses may be associated with a single index. Data store management system 925 may be located in a same or different geographic area than stream processing system 905, an event monitor 920 and/or one or more data-collection devices.

Data stores 915 may include one or more data stores. In some examples, the one or more data stores may include a resource scheduling allocation store 916, a routing protocol store 917, and a communication protocol store 918. Resource scheduling allocation protocol store 916 can include information corresponding to resource scheduling allocations associated with various devices in interaction system 900. For example, resource scheduling allocation store 916 may include a resource scheduling allocation associated with a navigator device (e.g., navigator device 110). A resource scheduling allocation may include a timetable that indicates that particular blocks of times have been assigned to (or held for) particular entities or uses and/or that other particular blocks of times remain available for assignment. The resource scheduling allocation may also indicate capacities for accepting new tasks during a particular time period. Routing protocol store 917 may include information corresponding to routing hierarchies and/or priorities associated with devices in interaction system 900. For example, routing protocol store 917 may include information identifying a particular navigator device to receive a particular data element. In this example, this information may indicate that particular data elements are to be routed to particular navigator device. Communication protocol store 918 may include information corresponding to communication protocols. For example, one or more communication protocols can be used to adjust a resource scheduling allocation associated with a navigator device. A communication protocol may include data representing a standard for adding tasks to resource scheduling allocations (e.g., a task may include initiation a communication attempt with a user). In some examples, a communication protocol may include data representing a decision tree or a workflow. The decision tree or the workflow can identify tasks to be completed by a navigator associated with a navigator device and a schedule for completing the tasks. Further, a communication protocol may include one or more communication triggers. A communication trigger may include an indication of a pending task and may be associated with a particular time. For example, a communication trigger may include data indicating that a task is to be completed on a given day at a given time (e.g., or within a given time period). It will be appreciated that the pending task indicated by the communication trigger may be included in the decision tree or the workflow of the communication protocol. For example, a pending task may be to initiate a communication attempt with a user communication device (e.g., a mobile phone) associated with a user.

Data store controller 930 may control access to one or more data stores in data stores 915. In some instances, data store controller 930 may query data from one or more data stores of data stores 915. For example, data store controller 930 may query communication protocol store 918 for a particular communication protocol. In other instances, data store controller 930 may grant or deny access of another device to the one or more data stores in data stores 915. For example, data store controller 930 may determine that a device is authorized to obtain information from data stores 915. Data store controller 930 may also control (e.g., save, delete, transfer) content within data stores 915.

Client device 940 may include one or more processors, one or more memories and one or more interfaces for communicating with other devices and/or receiving input. In some examples, client device 940 may be coupled to priority tag store 945, navigator routing system 950, and/or data store controller 930. Further, client device 940 may control the data included in the priority tag store 945, navigator routing system 950, and/or data store controller 930. For example, client device 940 may configure the set of priority tags included in priority tag store 945. In this example, client device 940 may communicate with priority tag store 945 to update the priority tags periodically or dynamically when necessary. Machine-learning techniques may be implemented to determine when the priority tag store 945 is to be updated.

Navigator routing system 950 may include one or more processors, one or more memories and one or more interfaces for communicating with other devices and/or receiving or transmitting data. Navigator routing system 950 may receive one or more data streams (e.g., data stream 955) from stream processing system 905. Navigator routing system 950 may process the one or more data streams to determine additional tasks to be completed and facilitate completion of the additional tasks.

In some examples, a data stream received at the navigator routing system 950 may include one or more data elements associated with a user communication device. A user communication device may be a device associated with a user (e.g., a patient). Examples of one or more user communication devices can include, for example, a computer, a mobile device, a smart phone, a laptop, an electronic badge, a set-top box, a thin client device, a tablet, a pager, and other similar user communication devices. For example, a data element may include a phone number associated with a user communication device (e.g., operated by the user).

Figure 10:
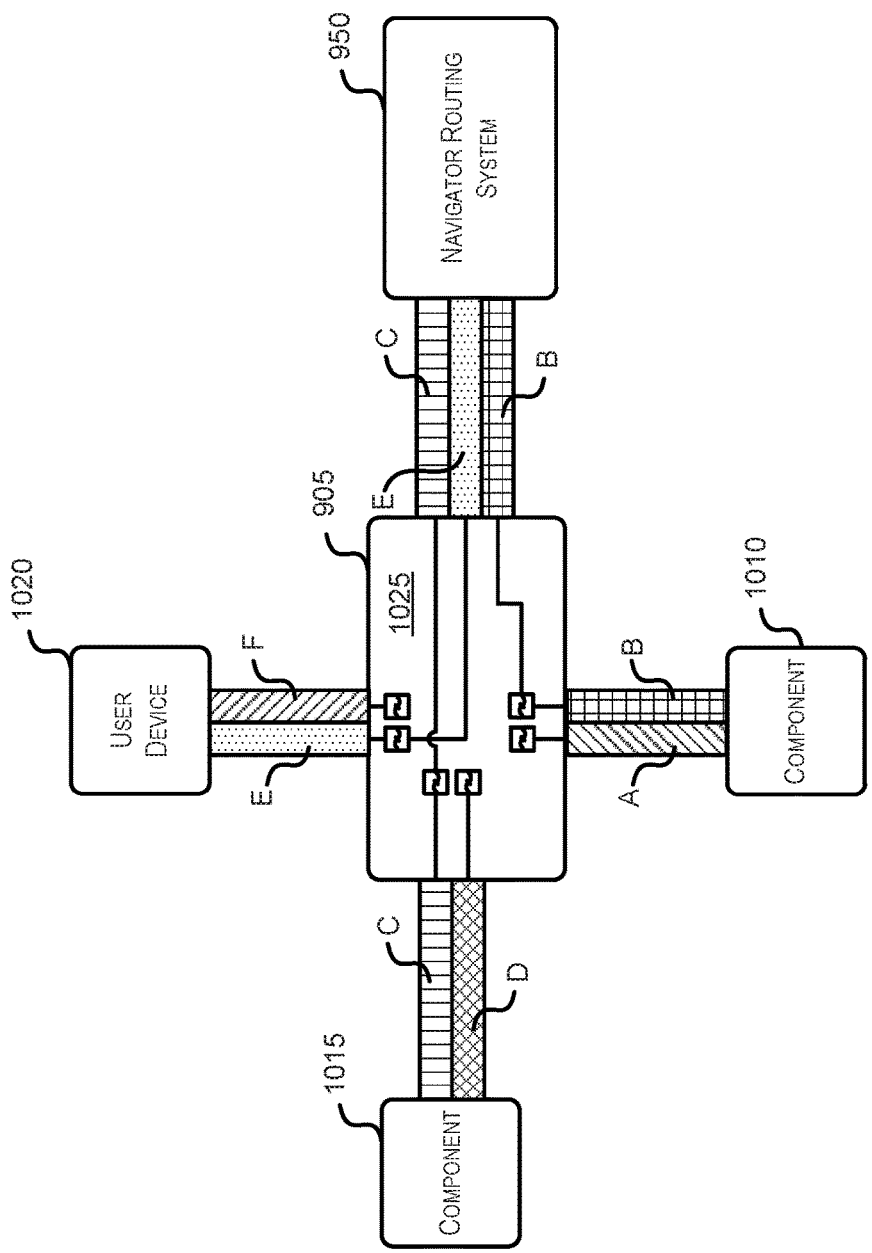
FIG. 10 shows an illustration of a processing flow of data streams according to an embodiment of the invention.

FIG. 10 shows an illustration of a process for intelligently processing the flow of data streams according to an embodiment of the invention. Stream processing system 905 may receive one or more data streams from various components and/or user devices. For example, stream processing system 905 may receive data streams A through F originating from components 1010 and 1015 and user device 1020.

Data streams A through F may include source data corresponding to various users. In some examples, data streams A through F may include source data corresponding to various conditions of users. For example, the source data of data streams A, D, and F may include information relating to users having a first type of condition (e.g., a low risk condition). In this example, parameters (e.g., measurements, attributes, lab results, etc.) corresponding to the first type of condition may be obtained at a facility (e.g., at components 1010, 1015 and/or user device 1020) and may be included in data streams A, D, and F. Data streams B, C, and E may include data corresponding to users having a second type of condition (e.g., a high risk chronic condition). In this example, parameters (e.g., measurements, attributes, results, etc.) corresponding to the second type of condition may be obtained at a facility (e.g., at components 1010, 1015 and/or user device 1020) and may be included in data streams B, C, and E.

Stream processing system 905 can receive a vast amount of data from various data sources (e.g., components 1010 and 1015 and/or user device 1020). In some examples, stream processing system 905 can process the vast about of data included in data streams A through F using rules or filters. For example, filters 1025 may filter out some data streams (e.g., data stream A, data stream D, and data stream F) and route other data streams (e.g., data stream C, data stream E, and data stream B) to navigator routing system 950. The data streams that are filtered out (e.g., data streams A, D, and F) may be stored (e.g., at data store management system 925) or forwarded to another destination. Data streams C, E, and B may also be stored and may be forwarded or routed to navigator routing system 950 for additional processing.

Filters 1025 may include rules to identify which data streams to route to navigator routing system 950 and which data streams are forwarded elsewhere or stored at data store management system 925. In some instances, filters 1025 may be configured to prioritize certain data streams over others. For example, filters 1025 may be configured by an administrator to prioritize data streams. Prioritizing data streams may include routing the data streams to navigator routing system 950 for additional processing. In other instances, filters 1025 may be dynamically determined using machine-learning techniques. For example, machine-learning techniques (e.g., data mining, machine-learned rules, machine-defined rules, machine-learning algorithms) may be implemented to mine data streams and predict or forecast patterns in the mined data. In this example, machine-learning techniques may be implemented to determine that data streams C, E, and B are of particular importance. For example, data streams C, E, and B may contain data corresponding to particular health conditions (e.g., high-risk conditions). Stream processing system 905 may then reconfigure filters 1025 to forward or route data streams C, E, and B and to store or route data streams A, D, and F to another destination. Filters 1025 may be dynamically configured and changed over time using, for examples, machine-learning techniques.

Navigator routing system 950 may receive data streams C, E, and B and perform additional processing on the received data streams. In some examples, navigator routing system 950 may identify and schedule workflows for users associated with data included in data streams C, E, and B.

It will be appreciated that filters 1025 can be used to route data streams to various destinations based on information associated with the data sources generating the data streams. Examples of information associated with the data sources can include error rates of data included in the data streams, error rates associated with the data source transmitting the data stream (e.g., error rates corresponding to a third-party provider associated with the data source), and other suitable error rates.

For example, user device 1020 can generate data included in data stream E, and the data can be associated with a high error rate (e.g., results or measurements that have a high error rate). Further, in this example, component 1015 can generate data, which is included in data stream C, and which is associated with a low error rate (e.g., results or measurements that have a low error rate). Component 1010 can correspond to a third-party provider that is associated with a high error rate (e.g., a third-party provider with a history of high error rates associated with the data generated at component 1010). Filters 1025 can be configured to route data streams having a high error rate (e.g., a high error rate associated with the data in the data stream and/or a high error rate associated with the data source transmitting the data stream) to navigator routing system 950. Navigator routing system 950 can generate workflows for navigator devices to follow-up on or review the data associated with high error rates.

Figure 11:
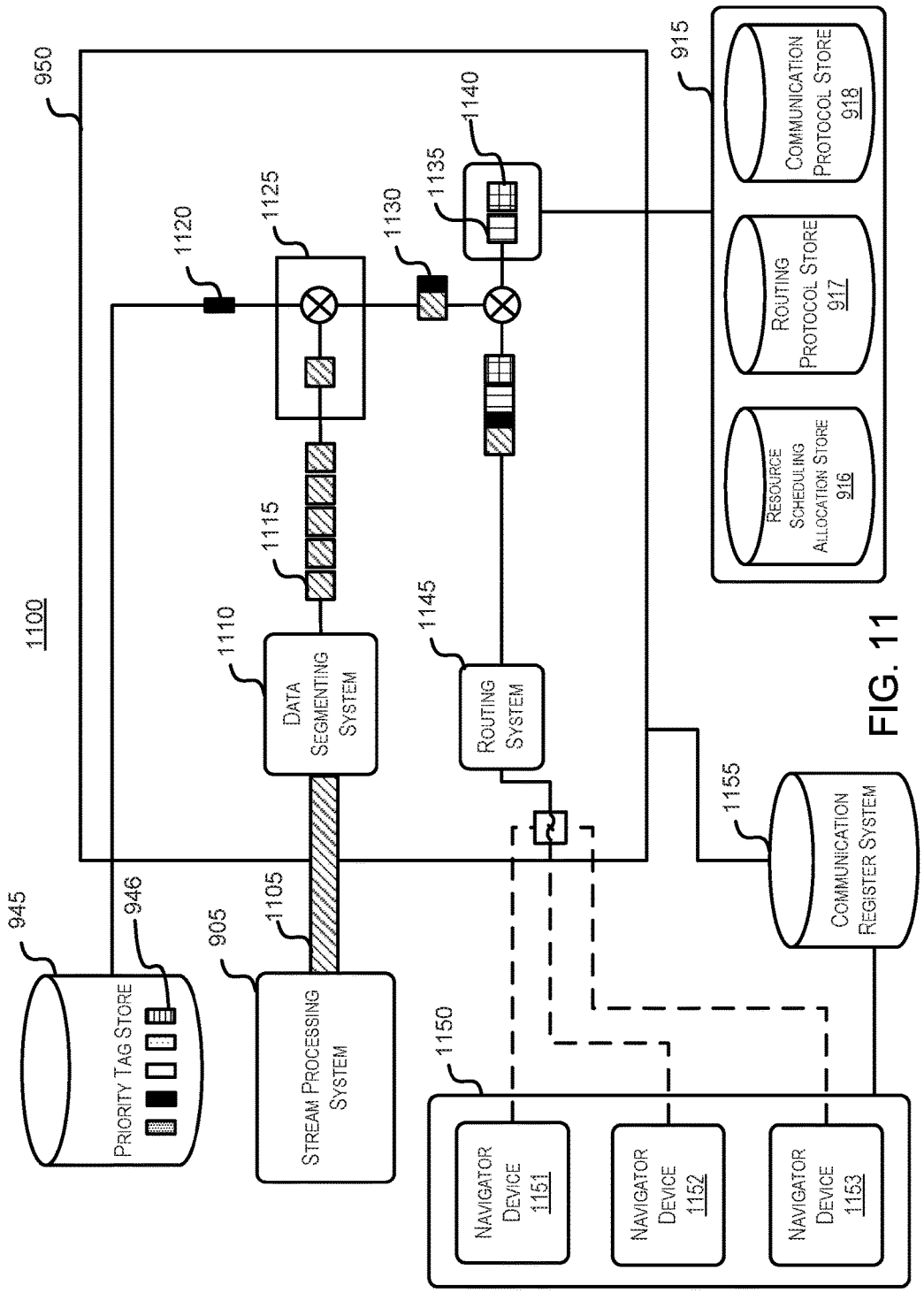
FIG. 11 shows an illustration of a processing flow of data elements according to an embodiment of the invention.

FIG. 11 shows an illustration of a processing flow of data elements in environment 1100 according to an embodiment of the invention. Environment 1100 may include at least stream processing system 905, navigator routing system 950, priority tag store 945, data stores 915, navigator devices 1150, and communication register system 1155.

Stream processing system 905 may receive one or more data streams and selectively filter the one or more data streams based on filter rules (e.g., filter 1025). The filtered data streams may be transmitted to navigator routing system 950 as incoming data stream 1105. The filtered data may include at least one data stream from the one or more data streams received at stream processing system 905 (as illustrated in FIG. 10). In some examples, additional data streams may be added to incoming data stream 1105 before being transmitted to navigator routing system 950. In these examples, these additional data streams may or may not originate from stream processing system 905.

Navigator routing system 950 can be configured to receive, transform, route and/or store data elements from one or more streams (e.g., incoming data stream 1105). Navigator routing system 950 may include, for example, data segmenting system 1110, data appendor 1125, and routing system 1145. In some examples, navigator routing system 950 can include or communicate with, for example, a transaction management engine (e.g., transaction management engine 106) and/or transformative processing engine (e.g., transformative processing engine 108).

Navigator routing system 950 may, in some instances, be remote from one, more or all sources of data streams being processed. Navigator routing system 950 may include one or more servers (e.g., a server farm) that may include a collection of specialized processing engines (e.g., each engine being a server or processing core). A processing engine may be specialized so as to include, for example, fast multi-lean memory buses (e.g., a 128-bit or 256-bit wide interconnections). A processing engine may be configured for bulk memory transfers. For example, a Stream Register File (SRF) can store stream data to be transferred to external data stores in bulks and specialized chips (e.g., the Imagine chip) can facilitate strategic flow and packing of the SRFs.

Incoming data stream 1105 may be received at data segmenting system 1110. Data segmenting system 1110 may include one or more data parsers to parse through incoming data stream 1105 and segment incoming data stream 1105 into individual data elements. In some examples, the one or more data parsers of data segmenting system 1110 can be configured to read incoming data stream 1105 and identify the beginning and/or end of individual data elements included in incoming data stream 1105. Each data element in incoming data stream 1105 may be assigned an index. Indices may be used to monitor whether and/or an extent to which data elements are being reliably received from stream processing system 905 or data sources. The indices may correspond to an order in which data elements are appended to the stream at the data sources. Thus, monitoring a stream-transmission reliability may then include detecting whether data elements corresponding to each of a set of sequential indices have been received. In some examples, indices may also be used to indicate a location within incoming data stream 1105 of a beginning position of a data element and/or an ending position of a data element. In these examples, the one or more data parsers can use the indices of the data elements to segment incoming data stream 1105 into individual data elements (e.g., data elements 1115).

Individual data elements 1115 can include data associated with a particular user. For example, an individual data element can include data related to a condition associated with a user (e.g., diagnostic results or measurements associated with the user). As another example, an individual data element can include data identifying a user communication device operated by the particular user (e.g., a phone number of a mobile device operated by a user).

In some examples, a data element may contain one or more composites (e.g., field of data). For example, one or more composites may contain data corresponding to the particular user communication device. The particular user communication device may be associated with the user. In some instances, a first composite within a data element may contain data indicating a condition associated with the user. For example, the first composite (e.g., a parameter composite) may contain data indicating a condition attributed to the user (e.g., a condition having a high severity). In some cases, the first composite may also include data associated with the condition attributed to the user (e.g., test results, measurements, lab reports, and the like). Data representing results or measurements can be included in one or more composites contained in an individual data element. In addition, a second composite within the data element may contain data that includes an additional representation of data included in the first composite. For example, the second composite (e.g., a condition composite) may include data identifying a severity of the user's condition, which is included in the first composite. In this example, the second composite within the data element may include the stage of the kidney condition (e.g., one of stages 1 through 5). In some examples, a data element may include a third composite, which may represent additional detail of the first and/or second composites. For example, in a particular data element, the third composite can include data representing an error rate corresponding to data associated with a condition attributed to the user. In this example, if a first composite includes lab results relating to a condition attributed to the user, the third composite can include an error rate associated with the results included in the first composite. In some examples, the error rate can be associated with the data source at which the result was generated. It will be appreciated that an individual data element can include any number of composites. Further, it will also be appreciated that data elements within a data stream may include the same number and types of composites as other data elements, or alternatively, data elements may include different numbers and types of composites from each other. It will also be appreciated that data associated with a particular user can span one or more data elements.

Individual data elements 1115 can be received at data appendor 1125. Data appendor 1125 can receive an individual data element and read data contained in one or more composites of the data element. Further, data appendor 1125 can transmit a query to priority tag store 945 to obtain a priority tag that corresponds to the data contained in the one or more composites of the data element. In some examples, data contained in the one or more composites may correspond to a specific priority tag stored in the priority tag store 945. For example, if a first composite in a data element includes data indicating a first condition and if a second composite in the same data element indicates that the first condition has a high severity, navigator routing system 950 can query priority tag store 945 for a priority tag that corresponds to the first condition having the high severity. As another example, navigator routing system 950 (e.g., via data appendor 1125) can query priority tag store 945 for a priority tag corresponding to a high priority.

A priority tag (e.g., priority tag 946) can include data representing a priority associated with a condition. The priority tag can include an item of data (e.g., a code) that can represent a priority assigned to the condition. When processed, the priority tag can indicate that the data contained in the corresponding data element is to be prioritized according to the priority associated with the priority tag. For example, a condition having a high severity can correspond to a priority tag that indicates a high priority. In this example, the high priority can be represented by a code that signals a high priority. The priority tag can be used as an indicator for evaluating how to process the data element appended to the priority tag. Using the example of a priority tag associated with a condition having a high severity, the priority tag can indicate to devices or systems that process the data element associated with the priority tag that the data element is designated a high priority. For an example of prioritizing data, see U.S. Ser. No. 14/172,736, filed on Feb. 4, 2014, the disclosure of which is hereby incorporated by reference in its entirety for all purposes.

The data appendor 1125 may query priority tag store 945 for a priority tag corresponding to one or any combination of the first composite, second composite, and third composite. In some examples, a data element may contain a third composite that includes data representing a high error rate. In these examples, data appendor 1125 may query priority tag store 945 for a priority tag that corresponds to a high error rate. For example, a test result associated with a high error rate may be treated as a high priority in navigator routing system 950 because the test result may require additional follow-up by a navigator. An additional follow-up by a navigator may reduce the chances of processing an erroneous test result or measurement. For example, if a test result has a high error rate, data appendor 1125 may query priority tag store 945 for a priority tag indicating a high priority. As a result, the priority tag may represent that urgent follow-up with the user by a navigator is necessary (e.g., by requesting that the test result be re-obtained or verified by a resource).

It will be appreciated that the first, second, and third composites in a data element may be included in the data element in any order. Further, it will be appreciated that, instead of an error rate associated with data, the third composite may include an indication of whether an abnormality exists in the test result or measurement (e.g., the test result included in the first or second composite). When an abnormality exists, and the abnormality is indicated in the third composite (e.g., by a code indicating an abnormality of the test result), data appendor 1125 may query priority tag store 945 for a priority tag that indicates a high priority. As a result, the priority tag may represent that urgent follow-up with the user by a navigator is necessary (e.g., by requesting that the test result be re-obtained or verified by a resource to solve the abnormality). It will also be appreciated that an abnormality of a test result or measurement may be determined by navigator routing system 950, rather than by being represented in the data elements (e.g., in the third composite). For example, the test result included in a data element may be compared against average values of test results of the same type to determine whether the test result is abnormal.

Priority tag store 945 may respond to the query for a priority tag with a selected priority tag. In some examples, priority tag store 945 may use a lookup table to select a priority tag based on the query from navigator routing system 950. For example, priority tag store 945 may query or scan a lookup table to identify a priority tag associated with a condition having a high severity. In some examples, priority tag store 945 may transmit an identification code (e.g., an identifier) of the priority tag to data appendor 1125. In these examples, data appendor 1125 receives the identifier and obtains the priority tag using the identifier. Data appendor 1125 may obtain or access the priority tag from priority tag store 945 or another data store (e.g., a local or remote data store). In other examples, priority tag store 945 may receive the priority tag in addition to or in lieu of the identifier. In further examples, data appendor may receive the identifier and append the identifier to the data element.

Appending the priority tag to the data element may include associating the priority tag to the data element. In some examples, the priority tag (e.g., or an identifier of the priority tag) may be added to the data contained within the data element. For example, the priority tag may be included within a composite at the end of the data element. It will be appreciated that the priority tag may be added to the beginning of the data element or to any position within the data element. In other examples, the priority tag may be segmented or divided and added at various positions within the data element. It will be appreciated that there are other techniques for associating priority tags with data elements.

A result of data appendor 1125 includes a data element appended to the selected priority tag (e.g., result 1130). Result 1130 may be transmitted to another data appendor (or this may occur within data appendor 1125) which can read the priority tag and identify additional data to append to result 1130 based on the priority tag. In some examples, navigator routing system 950 can identify or query data stores 915 for a communication protocol that corresponds to the priority tag. For example, a priority tag associated with a condition having a high severity indicates a high priority of processing. In this example, navigator routing system 950 can identify a communication protocol that similarly indicates a high priority of the data element (e.g., from communication protocol store 918). As another example, a priority tag associated with a data element that includes a test result or measurement having a high error rate may also indicate a high priority of processing. In this example, navigator routing system 950 can identify a communication protocol that similarly indicates a high priority of following up with the user associated with the data element.

Communication protocols can include a standard for adjusting a resource scheduling allocation associated with a navigator device. A communication protocol can correspond to a particular urgency or priority level. A communication protocol can include data representing a decision tree or workflow. The decision tree or workflow can identify tasks and/or a schedule for completing the tasks for a navigator. In some examples, a communication protocol can include one or more communication triggers. A communication trigger may include an indication for completing a task at a particular time. For example, a communication trigger may include an indication to initiate a communication attempt with a user communication device (e.g., a mobile device associated with a user) to schedule one or more follow-up sessions with a resource at a facility. The communication trigger can be configured to be added to a resource scheduling allocation. For example, a resource scheduling allocation may be adjusted to include a communication trigger. The communication trigger may indicate that a particular task is to be completed at a particular time (e.g., at 11:00 a.m. Eastern) or within a particular time period. For example, the particular task may include a task to initiate a communication attempt with a user communication device. It will be appreciated that a communication trigger can include data representing a task and a schedule for completing the tasks. For example, the data representing a schedule for completing the tasks can include a time slot to be included in a resource scheduling allocation associated with a navigator device.

Navigator routing system 950 may also identify a navigator device to associate with the data element. In some examples, a navigator device may be designated to facilitate performance of one or more tasks associated with a communication trigger. For example, navigator routing system 950 may identify a specific navigator device to perform or facilitate performance of initiating a communication attempt with a user communication device (e.g., a mobile phone associated with a user). The navigator device may be configured to perform the initiation of the communication attempt. In other examples, the navigator device may facilitate performance of the initiation of the communication attempt by identifying another device that is configured to perform the initiation of the communication attempt.

In some examples, navigator routing system 950 can identify a navigator device using the priority tag. For example, a priority tag may indicate that the appended data element is designated as a high priority. In this example, a navigator device may be selected from a plurality of navigator devices that is associated with high priority tasks. In other examples, a navigator device may be identified at random or based on one or more factors. Examples of factors may include resources currently available (e.g., nurses currently available), facility resources, time of day, time of year, condition associated with the data element, etc. Data blocks 1135 and 1140 may correspond to the identified communication protocol and the identified navigator device, respectively. Further, data blocks 1135 and 1140 may be appended to result 1130. Appending data blocks 1135 and 1140 to result 1130 may include adding data blocks 1135 and 1140 to any position within result 1130. In some examples, data blocks 1135 and 1140 may be segmented (e.g., divided) into smaller blocks and included in result 1130 at various positions.

Routing system 1145 may receive data blocks 1135 and 1140 and result 1130. Routing system 1145 may include one or more routers to route data blocks 1135 and 1140 and result 1130 to a navigator device. In some examples, navigator devices 1150 may be co-located (e.g., located within the same facility). In other examples, navigator devices 1150 may not be co-located, but rather, may be located at different facilities. Further, navigator devices 1150 may include navigator devices 1151, 1152, and 1153. Routing system 1145 may read data blocks 1135 and 1140 and result 1130 and extract data corresponding to the identified navigator device (e.g., data block 1140). Routing system 1145 may transmit the data blocks 1135 and 1140 and result 1130 to the identified navigator device. For example, if data block 1140 identifies navigator device 1151, routing system 1145 may transmit data blocks 1135 and 1140 and result 1130 to navigator device 1151. In some examples, routing system 1145 may compare data block 1140 with network addresses of navigator devices 1150. Upon finding a match, routing system 1145 may transmit data blocks 1135 and 1140 and result 1130 to the identified navigator device.

Navigator devices 1150 may facilitate communication attempts to user communication devices. Communication register system 1155 may determine whether a communication attempt has been performed. In some examples, communication register system 1155 may automatically detect whether a communication attempt has been performed. For example, communication register system 1155 may detect a signal transmitted by a navigator device upon initiating a communication attempt with a user communication device. In other examples, communication register system 1155 may determine that a communication attempt has occurred based on an input received from the navigator device. Communication register system 1155 may also individually track each navigator device to identify whether a particular navigator device has consistently failed to initiate communication attempts during a time period. It will be appreciated that communication register system 1155 can track other data related to occurrences of initiation attempts (e.g., whether the communication attempt was successful, time of communication with user communication device, etc.).

Figure 12A:
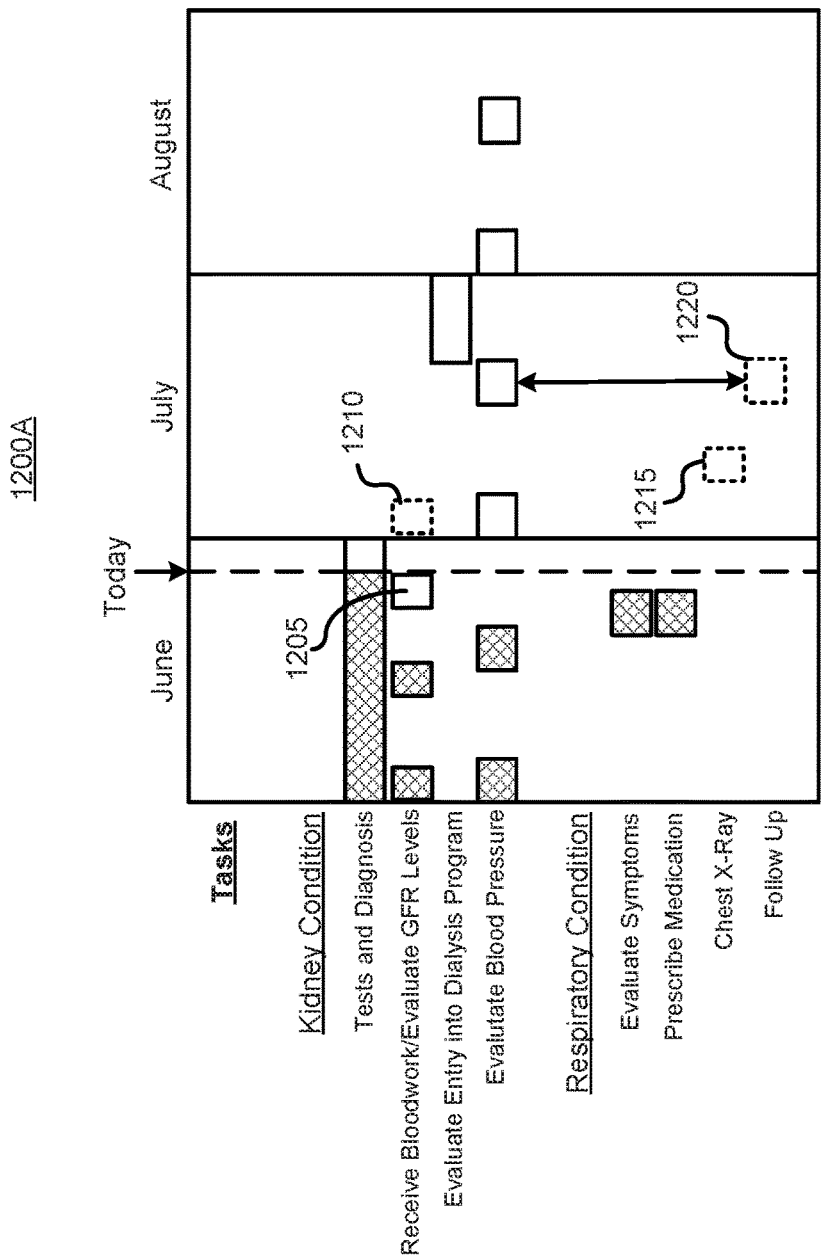
FIG. 12A shows an illustration of a resource scheduling allocation according to an embodiment of the invention.

FIG. 12A shows an illustration of a resource scheduling allocation 1200A according to an embodiment of the invention. In some examples, resource scheduling allocation 1200A may be associated with a particular navigator device, and may be stored in the particular navigator device or may be stored elsewhere (e.g., on a remote server) and accessed by the particular navigator device. In some examples, resource scheduling allocation 1200A may represent a schedule that indicates that particular blocks of times have been assigned to (or held for) particular resources or uses and/or that other particular blocks of times remain available for assignment. Resource scheduling allocation 1200A may also indicate availability for new tasks during a particular time period. In some examples, representation of resource scheduling allocation 1200A may be displayed on the particular navigator device.

In some examples, resource scheduling allocation 1200A may relate to a program for treating a user with respect to a condition (e.g., a severe condition). As shown in FIG. 12A, several tasks may be associated with the user's condition. For example, these tasks may be performed at various times between June and August. It will be appreciated that various tasks included in a resource rescheduling allocation may be performed at any time.

A navigator routing system (e.g., navigator routing system 950) may detect an instance 1205 where a task has not been completed (e.g., cross-hatched portions indicate completed tasks). In some examples, the navigator routing system may automatically detect that the task was not completed, for example, during a designated time period. For example, the navigator routing system may query a database for results of the task and identify that the results of the task are not available. In other examples, the navigator routing system may determine that the task was not completed based on an input received from a resource (e.g., a navigator device).

Further, for example, the user may have recently presented with an additional condition. Several tasks may be associated with the user's additional condition.

Further, in resource scheduling allocation 1200A, at the position indicated by "Today", the navigator routing system may identify three pending tasks to be completed. For example, the navigator routing system may determine tasks 1210 (e.g., reassign a time to complete instance 1205), 1215 (e.g., set a time for a session), and 1220 (e.g., set a time for a session) may be currently pending tasks.

The navigator routing system may automatically arrange the three pending tasks (e.g., tasks 1210, 1215, and 1220). For example, the navigator routing system may identify that task 1210 is associated with a higher priority than task 1215 (e.g., due to the condition associated with task 1210 having a higher priority than the condition associated with task 1215). Further, the navigator routing system can assign a time candidate for task 1210 that is an earlier time than a time candidate assigned to task 1215. A time candidate may include a proposed time assigned to the session or task. For example, the proposed time may be provided to the user for authorization. In addition, with respect to task 1220, the navigator routing system can identify that the user is already assigned a time in mid-July for a session related to another condition. The navigator routing system can automatically determine that task 1220 can be combined with the session in mid-July. For example, the navigator routing system can determine that task 1220 can be completed during the mid-July session, which is already assigned to the user for another condition. In this example, the navigator routing system may include an indication in resource scheduling allocation 1200A to complete task 1220 during the mid-July session. As a result, the navigator routing system may determine that a separate session for task 1220 may not be necessary, but rather, task 1220 can be performed during another session.

It will be appreciated that task 1205 may correspond to an abnormal lab result, rather than a result that is missing from a third-party provider. For example, if a result is not within an particular range, task 1205 may be a task to initiate a communication with a user or resource to verify the abnormal result. It will also be appreciated that task 1205 may include re-performing the test on the user to obtain an additional result.

Figure 12B:
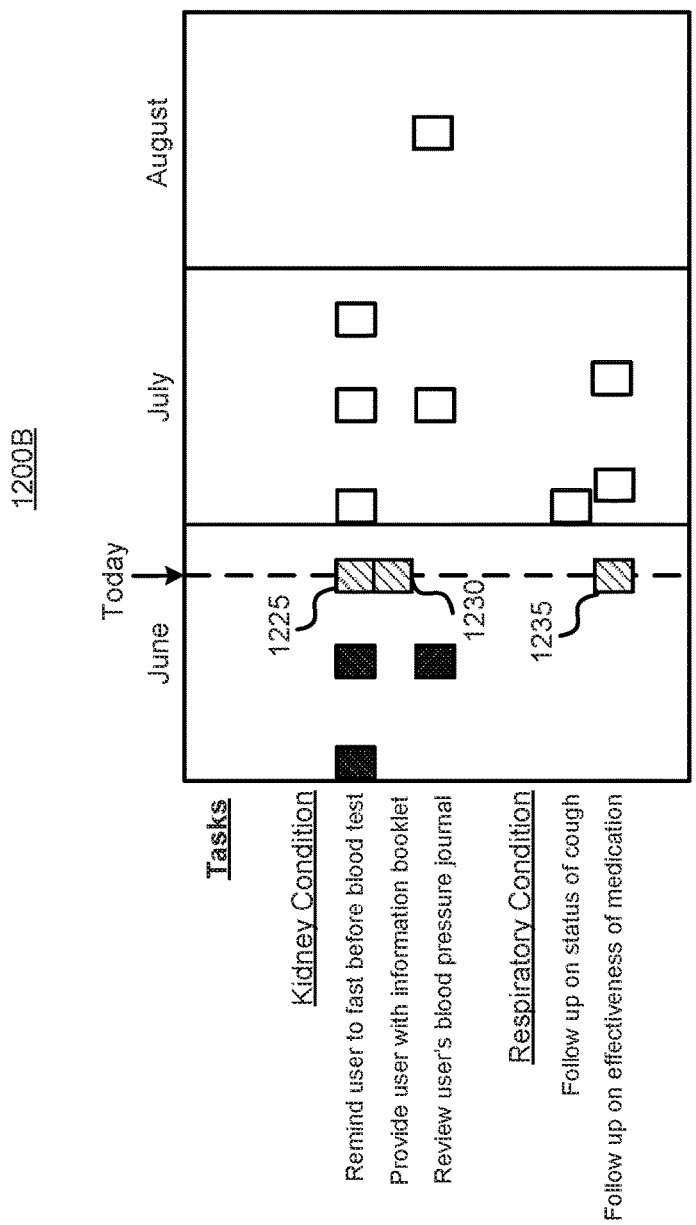
FIG. 12B shows an illustration of a resource scheduling allocation according to another embodiment of the invention.

FIG. 12B shows an illustration of a resource scheduling allocation 1200B according to another embodiment of the invention. In some examples, resource scheduling allocation 1200B may be associated with a particular navigator device.

For example, resource scheduling allocation 1200B may be stored in the navigator device or may be stored elsewhere (e.g., on a remote server) and accessed by the navigator device. Resource scheduling allocation 1200B may represent a schedule that indicates that particular blocks of times have been assigned to (or held for) particular resources or uses and/or that other particular blocks of times remain available for assignment. Resource scheduling allocation 1200B may also indicate availability for new tasks during a particular time period. In some examples, an interface corresponding to resource scheduling allocation 1200B may be displayed on the associated navigator device.

In some examples, resource scheduling allocation 1200B may indicate tasks that are associated with the user (e.g., solid black indicating a completed task, diagonal lines indicating a pending task, etc.). For example, a navigator routing system may automatically identify the tasks to be completed with respect to one or more conditions associated with the user. In addition, the navigator routing system may set times or time candidates for the identified tasks.

For example, a navigator routing system may detect that at a current time (e.g., "Today" in FIG. 12B) several tasks associated with the user's two conditions are pending. In this example, the navigator routing system may detect that a navigator device associated with a navigator is assigned a task of initiating a communication attempt with a user communication device to provide the user with certain information. The navigator routing system may adjust resource scheduling allocation 1200B associated with a navigator device to include the task. The navigator routing system can also detect additional tasks associated with the condition of the user. For example, the navigator routing system may adjust resource scheduling allocation 1200B associated with the navigator device to include task 1230. In some examples, a navigator device would be notified to initiate a communication attempt with the user regarding task 1225 and task 1230.

In addition, the navigator routing system can detect additional tasks related to other conditions that may be associated with the user. For example, the navigator routing system can detect that the user is associated with another condition. In this example, the navigator routing system can adjust resource scheduling allocation 1200B to include task 1235.

Identifying all tasks associated with the user with respect to various conditions and adjusting a resource scheduling allocation to include an indication of all of the tasks can be performed automatically by the navigator routing system. For example, in FIG. 12B, the resource scheduling allocation 1200B is adjusted to include all tasks (e.g., tasks 1225 and 1230 for a first condition and for a second condition) associated with the user. A navigator device can facilitate an initiation of a single communication attempt (e.g., a phone call) with a user communication device and effectively provide the user with all relevant information with respect to the various conditions associated with the user.

Figure 13:
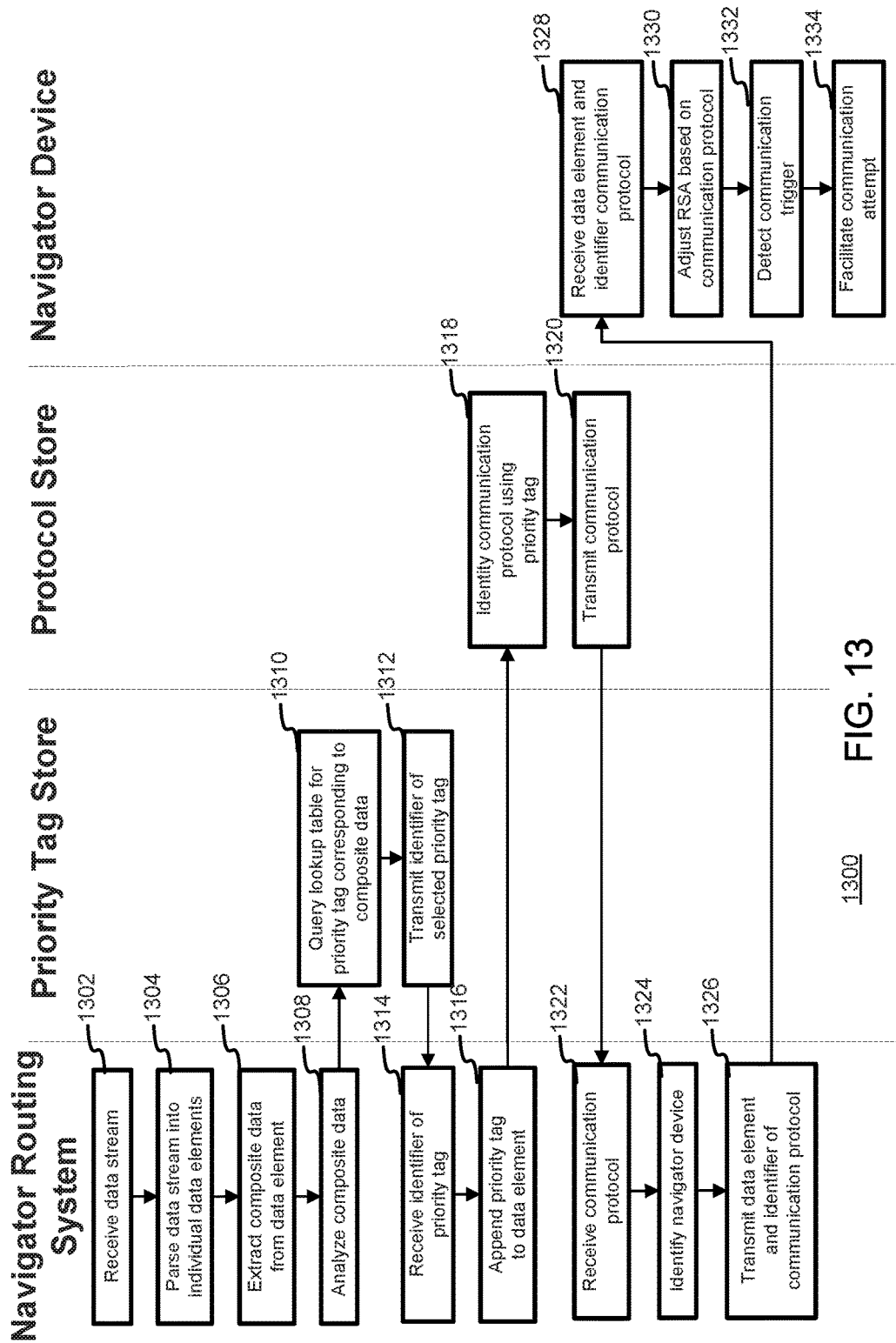
FIG. 13 shows a swim lane diagram of a process for processing data streams according to an embodiment of the invention.

FIG. 13 shows a swim lane diagram of a process 1300 for processing data streams according to an embodiment of the invention. Part or all of process 1300 may be performed, for example, at stream processing system 905, priority tag store 945, protocol store 918, data store management system 925, one or more navigator devices 1150, and/or navigator routing system 950. It will be appreciated that performance of process 1300 may be distributed. For example, various components of stream processing system 905, data store management system 925, one or more navigator devices 1150, and/or navigator routing system 950 (e.g., co-located components or geographically dispersed components) may perform different actions in process 1300.

At block 1302, the navigator routing system may receive one or more data streams. In some examples, the navigator routing system may receive a data stream from a stream processing system (e.g., stream processing system 905). The one or more data streams received at the navigator routing system may include data from various components and/or user devices 104.

At block 1304, a data stream of the one or more data streams may be parsed into individual data elements. In some examples, the data stream can be passed through a parser to parse the data stream into individual data elements. For example, a data stream may include a plurality of data elements. Each data element may include a code indicating the beginning and/or ending of a data element. When the data stream is passed through the parser, the parser may detect the code and determine the beginning and/or ending of a data element. The data stream may be converted into a data structure, such that the data structure includes data contained in the data elements. A data element may include one or more composites (e.g., fields).

At block 1306, the navigator routing system may read data of a particular data element and extract data from the one or more composites included in the data element. In some examples, a data element may include a composite corresponding to a condition associated with a user. The data element may also include a composite corresponding to a severity of the condition. In some examples, the data element may include a composite corresponding to an error rate associated with a test result or measurement for the user. At block 1308, the data extracted from the data elements is analyzed.

At block 1310, the navigator routing system may query a priority tag store (e.g., priority tag store 945) for a priority tag. In some examples, the navigator routing system may query a lookup table for a priority tag that corresponds to the analyzed data extracted from one or more composites of a data element. For example, if data extracted from a composite of the data element indicates a condition having a high-level of severity, then the navigator routing system may query a lookup table stored within the priority tag store for a priority tag that corresponds to the high-level of severity. The priority tag may represent the priority designated to data included in one or more composites of the data element. For example, the priority tag may represent the priority designated to a condition and/or the severity of the condition.

At block 1312, a result of the query is determined and an identifier of the selected priority tag is transmitted to the navigator routing system. In some examples, each priority tag may uniquely correspond to an identifier. For example, the identifier may include a code that is associated with a priority tag. In other examples, the priority tag store may transmit a priority tag to the navigator routing system in addition to, or in lieu of, the identifier.

At block 1314, the navigator routing system may receive the identifier of the selected priority tag. In some examples, upon receiving the identifier, the navigator routing system may access the priority tag associated with the received identifier. For example, the navigator routing system may access the priority tag from the priority tag store (e.g., priority tag store 945) using the identifier. In other examples, the navigator routing system may receive the priority tag with the identifier.

At block 1316, the priority tag is appended to the data element. In some examples, the navigator routing system may append the priority tag at the end of the data element. In other examples, the identifier may be appended to the data element, in addition to or in lieu of, the priority tag. It will be appreciated that the priority tag may be included at any position within the data element (e.g., at the beginning of the data in the data element, in the middle of the data in the data element, at the end of the data in the data element, etc.). It will also be appreciated that the priority tag may be divided into smaller parts and each part may be included in the data element at various positions.

At block 1318, the navigator routing system may identify a communication protocol using the priority tag. In some examples, the navigator routing system may access a communication protocol from a protocol store (e.g., communication protocol store 918). For example, a communication protocol that corresponds to the priority tag may be identified (e.g., using a lookup table). In this example, the communication protocol may include an urgent communication trigger for initiating a communication attempt with the user communication device.

At block 1320, the identified communication protocol is transmitted to the navigator routing system. In some examples, an identifier of the communication protocol is transmitted to the navigator routing system from a protocol store (e.g., communication protocol store 918). For example, an identifier may include a code that uniquely corresponds to the communication protocol. In other examples, the entire communication protocol may be transmitted to the navigator routing system. For example, data representing the communication protocol may be transmitted in addition to or in lieu of the identifier of the communication protocol.

At block 1322, the communication protocol is received at the navigator routing system. In some examples, when an identifier of the communication protocol is received at the navigator routing system, the navigator routing system may access data associated with the communication protocol from a server or data store (e.g., a local server or data store, a remote server or data store, etc.). In other examples, the navigator routing system may receive some or all of the data associated with the communication protocol.

At block 1324, a navigator device is identified. In some examples, the communication protocol may include data identifying a navigator device. For example, the communication protocol may identify a specific navigator device associated with the communication protocol, the priority tag, and/or one or more composites within the data element. In other examples, a navigator device or a set of navigator devices may be identified in advance. For example, a navigator device may be selected from amongst a set of navigator devices that are associated with the navigator routing system.

At block 1326, an identifier of the communication protocol and the data element are transmitted to the identified navigator device. In some examples, some or all of the data associated with the communication protocol can be transmitted together with the data element to the identified navigator device. The data element and the identifier of the communication protocol may be transmitted simultaneously or at different times.

At block 1328, the identified navigator device may receive the data element and the identifier of the communication protocol. In some examples, the navigator device may access a server (local or remote) for the communication protocol using the identifier. In other examples, the navigator device may retrieve the communication protocol from internal storage devices (e.g., non-volatile memory). In further examples, the navigator device may receive the communication protocol in addition to or in lieu of the identifier. Upon receiving the identifier, the communication protocol, and/or the data element, the navigator device may store the identifier, the communication protocol, and/or the data element. The navigator device may also forward the identifier, the communication protocol, and/or the data element to a storage device (local or remote).

At block 1330, a resource scheduling allocation (RSA) associated with the identified navigator device may be adjusted based on the communication protocol. In some examples, each navigator device may be associated with a resource scheduling allocation. For example, the resource scheduling allocation may identify capacities of a resource to accept tasks during particular time periods. Resource scheduling allocations may also indicate time periods of availability of a resource. Adjusting a resource scheduling allocation may include adding one or more tasks to the resource scheduling allocation. For example, a resource scheduling allocation may be adjusted by adding an indication to complete a particular task at a particular time (e.g., a task of initiating a communication attempt "today").

The communication protocol can include one or more communication triggers. A communication trigger may include an indication to complete a task at a particular time. A resource scheduling allocation may be adjusted to include the one or more communication triggers included in the communication protocol. For example, a communication trigger may indicate a task for initiating a communication attempt with a user communication device on a specific time and day. A resource scheduling allocation may be adjusted to include the communication trigger. The communication trigger may be included in a resource scheduling allocation at a given time and/or may indicate a task to be completed at another given time. The adjusted resource scheduling allocation may include an indication (at a given time or time period) to complete a task associated with the communication trigger (at the given time or another given time).

At block 1332, the communication trigger is detected. For example, a current time in a resource scheduling allocation may correspond to a time to indicate a task associated with the communication trigger. In this example, when a current time corresponds to a time associated with a communication trigger, the communication trigger may be detected. In some examples, an indication to complete the task associated with the communication trigger may be displayed at the navigator device. It will be appreciated that the indication to complete the task associated with the communication trigger may be exhibited in various ways. For example, a navigator device may output a sound, vibrate, present a notification, etc. In some examples, the communication trigger may indicate that a task is to be completed at a current time. For example, the communication trigger may indicate that an initiation of a communication attempt with a user communication device is to be performed at a current time. In other examples, the communication trigger may indicate that a task is to be completed at a later day or time, over a specific time period (e.g., within two hours), etc.

The task to be completed may include additional information associated with a user communication device. For example, the additional information may include, for example, notations for reminders, instructions for performing a test at a facility, indications to request follow-up information, etc. It will be appreciated that the additional information is not limited to these examples.

At block 1334, the navigator device may facilitate a communication attempt with a user communication device. In some examples, a communication attempt may include initiating a phone call to the user communication device. Additional examples of communication attempts may include transmitting a text message, video call, voice over Internet Protocol (VOIP) call, etc.

Figure 14:
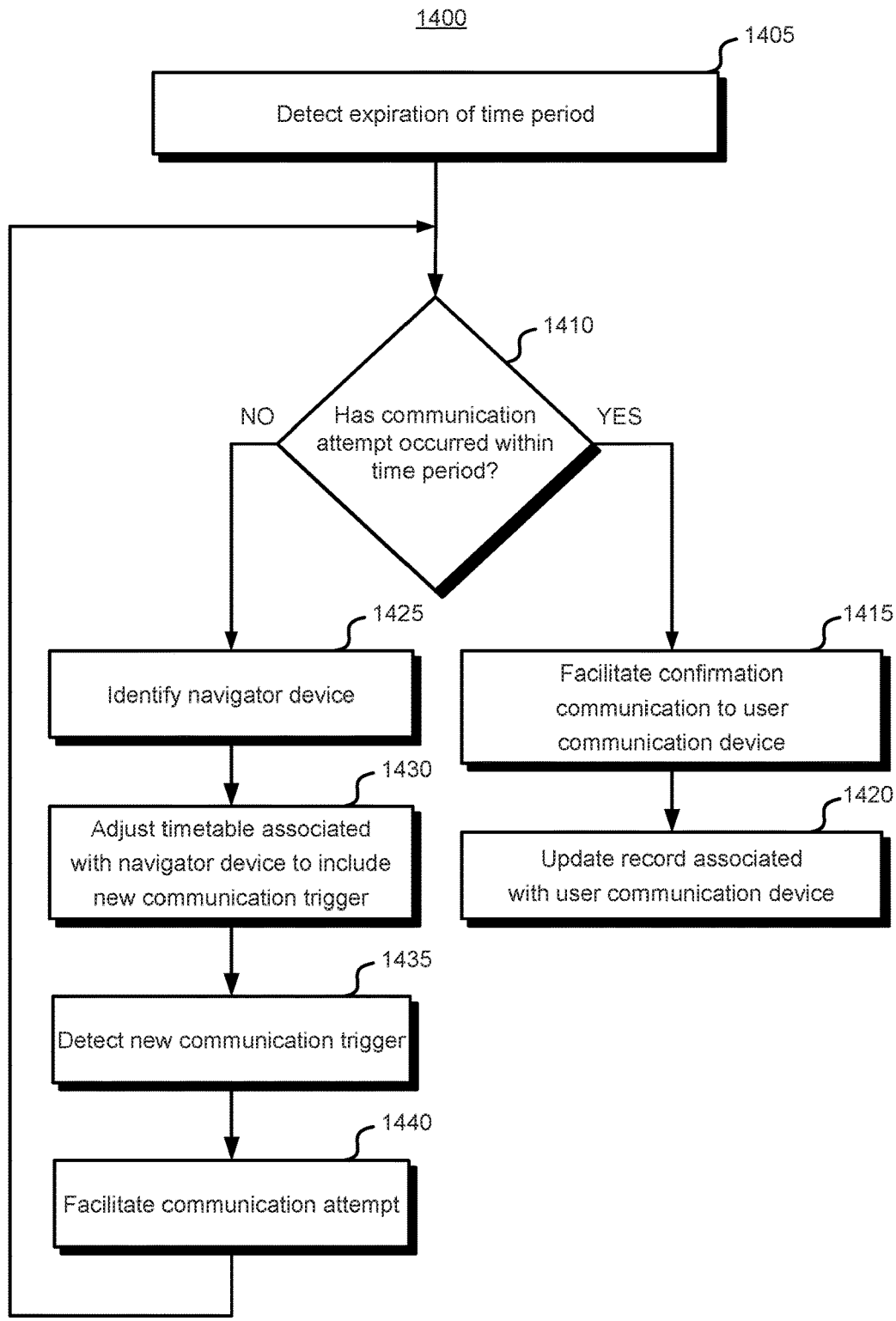
FIG. 14 shows a flowchart of a process for facilitating an initiation of a communication according to an embodiment of the invention.

FIG. 14 shows a flowchart of a process 1400 for facilitating an initiation of a communication according to an embodiment of the invention. Part or all of process 1400 may be performed, for example, at stream processing system 905, data store management system 925, one or more navigator devices 1150, and/or navigator routing system 950. It will be appreciated that performance of process 1400 may be distributed. For example, various components of stream processing system 905, data store management system 925, one or more navigator devices 1150, and/or navigator routing system 950 (e.g., co-located components or geographically dispersed components) may perform different actions in process 1400.

At block 1405, an expiration of a time period may be detected. In some examples, the time period begins upon detection of the trigger occurring. For example, block 1405 may follow block 1334 of FIG. 13. In some examples, the time period may be a preset time period (e.g., one hour, two hours, etc.) after the trigger has occurred. In other examples, the time period may also be determined dynamically. For example, a determination of the time period may depend on several factors, including one or more protocols, availability of resources (e.g., computational resources, equipment resources, laboratory resources and/or human resources), and severity of a condition associated with a user. In further examples, the time period may be periodic (e.g., every night at midnight, every morning, etc.). Upon detection of the expiration of the time period, process 1400 proceeds to block 1410.

At block 1410, the navigator routing system may determine whether or not the communication attempt with the user communication device has occurred within the time period. In some examples, the navigator routing system may make this determination based on a received input. For example, a navigator device may transmit a communication to the navigator routing system upon executing the communication attempt with the user communication device. The communication may be transmitted from the navigator device based on an input received at the navigator device or based on an automatic detection of the execution of the communication attempt at the navigator device. In other examples, the navigator routing system may automatically detect whether or not the communication attempt with the user communication device has occurred before the expiration of the time period. For example, the navigator routing system may automatically detect that a phone call has been made to the user communication device.

If the navigator routing system determines that the communication attempt has occurred ("YES" at block 1410), then process 1400 proceeds to block 1415. At block 1415, the navigator routing system facilitates a confirmation communication to the user communication device. In some examples, the navigator routing system may cause a transmission of a confirmation communication to the user communication device. For example, the navigator routing system may transmit a signal to a navigator device, causing the navigator device to transmit the confirmation communication to the user communication device. The confirmation communication may be transmitted via a device-to-device communication. For example, the confirmation communication may be transmitted via a message service (e.g., SMS) from a navigator device to the user communication device. In other examples, the confirmation communication may be transmitted over a network via an email service.

In some examples, the confirmation communication may include information associated with the initiation of the communication attempt. For example, the confirmation communication may include information corresponding to the time and date of the initiation of the communication attempt. As another example, the confirmation communication may include an indication of whether or not the communication attempt was successful in contacting or reaching the user communication device. As yet another example, when the communication attempt successfully reached the user communication device (e.g., the user communication device was available, a user associated with the user communication device was available, etc.), the confirmation communication may include information corresponding to a time assignment assigned to the user communication device. The time assignment is further described below with respect to FIG. 15.

At block 1420, a record associated with the user communication device is updated. In some examples, a record associated with the user communication device may be updated with the information included in the confirmation communication. In other examples, a record associated with the user communication device may be updated to include information associated with the confirmation communication. For example, the information associated with the confirmation communication may include a time and date of the transmission of the confirmation communication.

Referring back to block 1410, when the navigator routing system determines that the communication attempt has not occurred before expiration of the time period ("NO" at block 1410), then process 1400 proceeds to block 1425. At block 1425, a navigator device is identified. In some examples, the same navigator device previously identified in block 1324 (see FIG. 13) may be identified at block 1425. In other examples, a different navigator device may be identified at block 1425 than the navigator device identified at block 1324 of FIG. 13.

The navigator device identified at block 1425 may be based on a communication protocol (e.g., a communication protocol identified at block 1318 of FIG. 13). In some examples, a communication protocol may indicate a high-level of urgency for initiating a communication attempt with the user communication device. In these examples, if the communication attempt has not occurred before the expiration of the time period, then a new navigator device may be identified for initiating the communication attempt with the user communication device. In other examples, a communication protocol may indicate a low-level of urgency for initiating a communication attempt with the user communication device. In these examples, if the communication attempt has not occurred before the expiration of the time period, then the same navigator device may be identified for initiating additional communication attempts.

At block 1430, a resource scheduling allocation associated with the navigator device (identified at block 1425) may be adjusted to include a new communication trigger. In some examples, adjusting a resource scheduling allocation may correspond to including or adding a communication trigger to the resource scheduling allocation. The new communication trigger may indicate or signal to the navigator device that a communication attempt is to be made to the user communication device. For example, a communication trigger may indicate that a communication attempt is to be made to a user communication device.

In some examples, a new communication trigger may be determined based on a communication protocol (e.g., a communication protocol identified at block 1318 of FIG. 13). In some examples, a communication protocol may indicate a high-level of urgency for initiating a communication attempt with the user communication device. In these examples, if the communication attempt has not occurred before the expiration of the time period, then a new communication trigger may indicate that a next communication attempt to be made with urgency. For example, a new communication trigger may include a representation that the next communication attempt to the user communication device is to be performed in two hours, 4 hours, the next morning, etc. In other examples, a communication protocol may indicate a low-level of urgency for initiating a communication attempt with the user communication device. In these examples, if the communication attempt has not occurred before the expiration of the time period, then a new communication trigger may indicate that a next communication attempt to be made with without urgency. For example, a new communication trigger may include a representation that the next communication attempt to the user communication device is to be performed in one week, two weeks, etc.

At block 1435, the new communication trigger is detected. In some examples, the new communication trigger is detected at a specific time in the adjusted resource scheduling allocation. For example, a resource scheduling allocation associated with a navigator device can be adjusted to include a communication trigger indicating that a communication attempt is to be performed in one month and in three months. In this example, the navigator device may detect the new communication trigger at the one month point. The navigator device may also detect the new communication trigger at the three month point.

At block 1440, the navigator device may facilitate an initiation of a communication attempt. In some examples, the communication attempt can be initiated by transmitting a communication to the user communication device. For example, a communication attempt can be a phone call to the user communication device. A navigator device may initiate the phone call to the user communication device. Additional examples of communication attempts may include e-mailing an address associated with the user communication device, transmitting a message using a message service (e.g., Short Message Service (SMS), text message, etc.), and the like. It will be appreciated that devices other than the navigator device may initiate the communication attempt (e.g., a phone call) to the user communication device.

Figure 15:
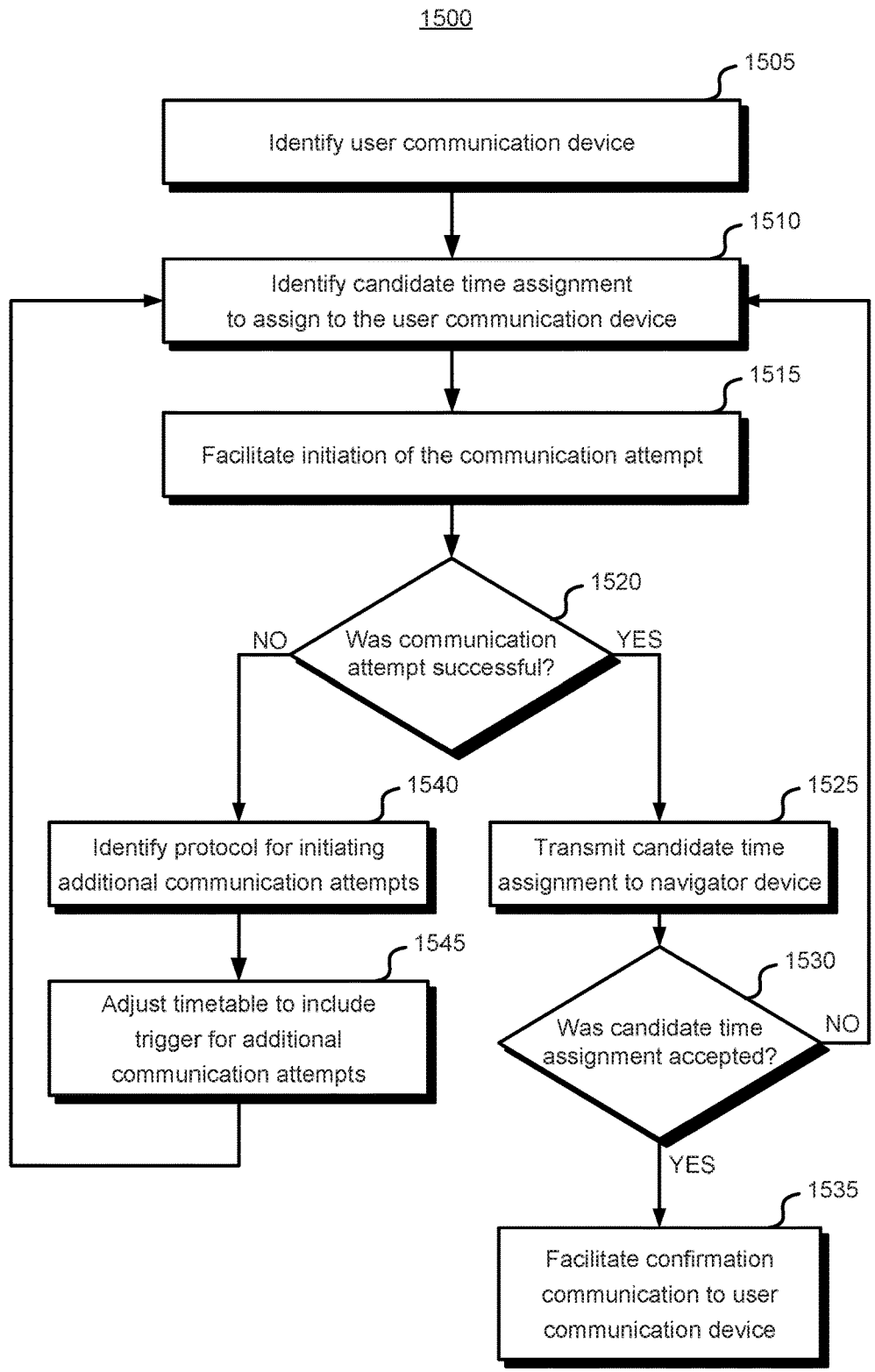
FIG. 15 shows a flowchart of a process for facilitating an initiation of a communication according to another embodiment of the invention.

FIG. 15 shows a flowchart of a process 1500 for facilitating an initiation of a communication according to another embodiment of the invention. Part or all of process 1500 may be performed, for example, at stream processing system 905, data store management system 925, one or more navigator devices 1150, and/or navigator routing system 950. It will be appreciated that performance of process 1500 may be distributed. For example, various components of stream processing system 905, data store management system 925, one or more navigator devices 1150, and/or navigator routing system 950 (e.g., co-located components or geographically dispersed components) may perform different actions in process 1500.

At block 1505, a user communication device is identified. In some embodiments, information identifying a device associated with a user can be identified. For example, a user communication device can be a mobile phone associated with a user, and information identifying the mobile phone can be a phone number. Additional examples of information identifying a user communication device can include a MAC address, an email address, a pager number, a network address, and the like.

The information identifying the user communication device can be extracted from one or more composites included in a data element. For example, a data element associated with a user communication device can be processed and pertinent information relating to the identification of the user communication device can be extracted. In other embodiments, an identifier of a user communication device can be included in one or more composites of a data element. Upon extracting the identifier of the user communication device, the navigator routing system can access a server to obtain additional information identifying the user communication device. The server can be local (e.g., as part of the navigator routing system) or remote. For example, the identifier of a user communication device can be a code extracted from one or more composites of a data element. The navigator routing system can query a server using the code to obtain additional information (e.g., a phone number) that identifies the user communication device.

At block 1510, a candidate time assignment can be identified and assigned to the user communication device. A candidate time assignment can include a time or a block of time to be assigned to the user communication device. The block of time can correspond to an appointment time to assign to a user associated with the user communication device. For example, the candidate time assignment can include an indication of time of 9:00 AM (Eastern Standard Time) that is assigned to the user communication device. In another example, the candidate time assignment can include an indication of a time block of 9:00 AM to 11:00 AM (Eastern). It will be appreciated that the candidate time assignment can include one or more times and/or one or more blocks of time.

In some embodiments, the candidate time assignment can be selected from a plurality of time assignments as a candidate to assign to the user communication device. For example, the navigator routing system can select a candidate time assignment that is the closest in time to a current time. In this example, the candidate time assignment would be a next available time assignment.

In other embodiments, the candidate time assignment may be determined using machine-learning techniques. For example, historical data associated with the user communication device can be mined to predict a candidate time assignment. The historical data can include information corresponding to previous time assignments assigned to the user communication device. The historical data can also include information corresponding to whether a user associated with the user communication device met with a resource at a time block corresponding to a previous time assignment or not. In this example, the candidate time assignment may include a predicted time assignment based on the user's previous time assignments. For example, if the user is historically assigned a time assignment of 9:00 AM (Eastern), the candidate time assignment can be identified as 9:00 AM (Eastern), as well. As a further example, if the user has previously been assigned various time assignment, and if the user has most often attended time assignments in the afternoon, the candidate time assignment can be identified as a time assignment in the afternoon. It will be appreciated that the candidate time assignment can be determined based on additional data, for example, availability of components (e.g., components 102 in facility 110), availability of resources (e.g., computational resources, equipment resources, laboratory resources and/or human resources), and the like.

At block 1515, the navigator routing system may facilitate an initiation of a communication attempt with the identified user communication device. In some examples, the navigator routing system can facilitate the initiation of the communication attempt by adjusting a resource scheduling allocation associated with a navigator device to include an indication of the identified candidate time assignment. For example, the resource scheduling allocation associated with the navigator device may be adjusted to include a trigger that signals the navigator device or a navigator associated with the navigator device to initiate a communication attempt with the user communication device.

In some examples, the communication attempt can be initiated by transmitting a communication to the user communication device. For example, a communication attempt can be a phone call to the user communication device. A navigator device may initiate the phone call to the user communication device. Additional examples of communication attempts may include e-mailing an address associated with the user communication device, transmitting a message using a message service (e.g., Short Message Service (SMS), text message, etc.), and the like. It will be appreciated that devices other than the navigator device may initiate the communication attempt (e.g., a phone call) to the user communication device.

At block 1520, the navigator routing system may determine whether or not the communication attempt with the user communication device was successful. In some examples, the navigator routing system may determine whether or not the communication attempt reached the user communication device. The navigator routing system may also determine whether or not a response to the communication attempt was received from the user communication device. For example, the navigator routing system may determine whether a phone call, initiated by a navigator device, was answered at the user communication device.

In some examples, the navigator routing system may determine that the communication attempt was successful based on an input received from a navigator device. For example, if the communication attempt was successful, the navigator device may transmit an indication of the successful attempt to the navigator routing system. In other examples, the navigator routing system may automatically determine that the communication attempt was successful based on a detection of the initiation of the communication attempt (e.g., a detection of a phone call initiated to the user communication device, a detection of an email or text message transmitted to the user communication device, and the like). In addition, data associated with an initiation of a communication attempt may be tracked and stored. For example, data including whether or not the communication attempt was made, and whether or not the communication attempt was successful may be tracked and stored (e.g., in communication register system 1155).

If the communication attempt at block 1520 was successful, then process 1500 proceeds to block 1525. At block 1525, the candidate time assignment is transmitted to the navigator device. In some examples, the candidate time assignment may be transmitted to the navigator device upon a successful communication attempt. In other examples, the candidate time assignment may be transmitted to the navigator device at an earlier time (e.g., during the facilitation of the initiation of the communication attempt at block 1515).

At block 1530, the navigator routing system may determine whether or not the candidate time assignment was accepted by a user associated with the user communication device. In some examples, the navigator routing system may determine whether or not the candidate time assignment was accepted based on a communication received from a navigator device. For example, the communication transmitted by the navigator device may indicate whether or not the candidate time assignment was accepted. In other examples, the navigator routing system may automatically determine whether or not the candidate time assignment was accepted. For example, an acceptance of the candidate time assignment may be determined based on a communication received from the user communication device (e.g., by detecting a signal corresponding to an acceptance, received from the user communication device).

If the navigator routing system determines that the candidate time assignment was not accepted at block 1530, then process 1500 proceeds back to block 1510, where a new candidate time assignment is determined. If the candidate time assignment was accepted at block 1530, then process 1500 proceeds to block 1535. At block 1535, the navigator routing system facilitates a transmission of a confirmation communication to the user communication device. In some examples, the navigator routing system may transmit a message to the user communication device using a message service (e.g., via SMS), email service, and the like. It will be appreciated that the navigator routing system may facilitate the transmission of the confirmation message using other transmission methods.

In some embodiments, a navigator device may transmit the confirmation message to the user communication device. The initiation of the transmission device may be automatic (e.g., automatically transmitted to the user communication device upon acceptance of the user communication device) or may be based on an input received at the navigator device. The confirmation communication may include an indication of the candidate time assignment.

Referring again to block 1520, if the navigator routing system determines that the communication attempt was not successful, then process 1500 proceeds to block 1540. At block 1540, a protocol for initiating additional communication attempts may be identified. In some examples, the navigator routing system may facilitate a query of a server or data store, which stores protocols. In these examples, the server may be queried using an identifier, which corresponds to a protocol for initiating additional communication attempts. In other examples, the protocol for initiating additional communication attempts may already be stored within the navigator routing system. For example, the protocol for initiating additional communication attempts may be included in a communication protocol previously identified by the navigator routing system.

The protocol identified at block 1540 may be selected based on one or more composites included in a data element associated with the user communication device. For example, the data element associated with the user communication device may include a composite that includes a representation of a condition of the user or a severity of a condition of the user. In this example, when the severity of the condition is high, a specific protocol corresponding to high-severity conditions may be identified. The protocol corresponding to high-severity conditions may include triggers associated with initiating one or more additional communication attempts urgently or as soon as possible. In other examples, the composite of a data element may include a representation of a condition having a low severity. In these examples, a specific protocol corresponding to low-severity conditions may be identified. The protocol corresponding to low-severity conditions may include triggers associated with initiating one or more additional communication attempts with low urgency.

At block 1545, a resource scheduling allocation associated with the navigator device may be adjusted to include additional triggers associated with the protocol identified at block 1540. In some examples, adjusting a resource scheduling allocation may include adding triggers to the resource scheduling allocation to signal a particular event. For example, an additional trigger may be added to a resource scheduling allocation of a current day. In this example, the additional trigger may include a representation of one or more communication attempts to be made during the current day. After block 1545, process 1500 proceeds back to block 1510, where a new candidate time assignment is assigned to the user communication device.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A system for automatically adjusting calendar schedules to facilitate initiations of communication attempts with patient communication devices, the system comprising:
one or more data sources that transmit source data;
a stream processor that:
receives the source data, and
generates one or more data streams using the source data, each data stream of the one or more data streams including a plurality of data elements, each data element of the plurality of data elements including a first composite, a second composite, and a third composite, the first composite representing a condition of a patient, the second composite representing a severity of the condition, and the third composite representing an error rate corresponding to data associated with the condition of the patient represented by the first composite; and
a hospital communication server associated with a hospital facility, the hospital communication server being configured to, for a data stream of the one or more data streams:
parse the data stream into one or more individual data elements,
extract information from a first composite, a second composite, and a third composite of an individual data element of the one or more individual data elements,
identify a patient communication device using the extracted information from the first composite and the second composite of the individual data element, each of the patient communication device and the individual data element being associated with a patient, the patient communication device being a computer, a mobile device, a smart phone, a laptop, an electronic badge, a set-top box, a thin client device, a tablet, or a pager,
query a lookup table using the second composite and the third composite,
identify a priority tag based on a result of the query,
associate the priority tag to the individual data element,
identify a communication protocol associated with the priority tag, the communication protocol including a first communication trigger for a first target task associated with the condition of the patient represented by the first composite,
identify a first navigator device based on the source data, the first navigator device being associated with a first calendar schedule of a nurse or a physician,
automatically adjust the first calendar schedule to include the first communication trigger;
automatically determine a first candidate time assignment to assign to the first target task, each of the first composite and the second composite of the individual data element being used to automatically determine the first candidate time assignment, and the first candidate time assignment corresponding to a first proposed appointment time for the patient,
detect that the first communication trigger has occurred based on the first calendar schedule,
facilitate an initiation of a first communication attempt from the first navigator device to the patient communication device according to the first communication trigger, the first communication attempt including the first candidate time assignment, and
determine whether the initiation of the first communication attempt has occurred within a defined time period, wherein when the initiation of the first communication attempt has not occurred within the defined time period, a second calendar schedule associated with a second navigator device is automatically adjusted to include a second communication trigger for the first target task, and the second navigator device initiates a second communication attempt from the second navigator device to the patient communication device,
wherein if the error rate is greater than a threshold, the priority tag and the associated communication protocol indicate a high priority of facilitating the initiation of the first communication attempt from the first navigator device to the patient communication device, and the first communication attempt includes a follow-up to address the error rate.

2. The system for automatically adjusting calendar schedules to facilitate initiations of communications with patient communication devices as recited in claim 1, wherein the hospital communication server is further configured to:
adjust the first calendar schedule associated with the first navigator device to include the first target task.

3. The system for automatically adjusting calendar schedules to facilitate initiations of communications with patient communication devices as recited in claim 1, wherein the second composite includes a representation of the first composite, the representation including additional information associated with the first composite.

4. The system for automatically adjusting calendar schedules to facilitate initiations of communications with patient communication devices as recited in claim 1, wherein the hospital communication server is further configured to:

when it is determined that the initiation of the first communication attempt has occurred, transmit a confirmation communication to the patient communication device, the confirmation communication including information associated with the initiation of the first communication attempt; and update a record associated with the patient communication device with the information associated with the initiation of the first communication attempt.

5. The system for automatically adjusting calendar schedules to facilitate initiations of communications with patient communication devices as recited in claim 1, wherein the hospital communication server is further configured to:

when it is determined that the initiation of the first communication attempt has not occurred within the defined time period, identify the second navigator device;

detect that the second communication trigger has occurred; and facilitate the second communication attempt with the patient communication device.

6. The system for automatically adjusting calendar schedules to facilitate initiations of communications with patient communication devices as recited in claim 1, wherein the hospital communication server is further configured to:

determine whether the first candidate time assignment was accepted by the patient associated with the patient communication device;

when it is determined that the first candidate time assignment was accepted, facilitate transmitting a final confirmation communication to the patient communication device; and when it is determined that the first candidate time assignment was not accepted, identify a new candidate time assignment to assign to the patient communication device.

7. The system for automatically adjusting calendar schedules to facilitate initiations of communications with patient communication devices as recited in claim 1, wherein the hospital communication server is further configured to:

when it is determined that the initiation of the first communication attempt was not successful, identify a protocol for initiating additional communication attempts with the patient communication device; and adjust the first calendar schedule to include one or more additional communication triggers for the additional communication attempts.

8. A computer-implemented method for automatically adjusting calendar schedules to facilitate initiations of communication attempts with patient communication devices, comprising:

receiving source data from one or more sources;

generating one or more data streams using the source data, each data stream of the one or more data streams including a plurality of data elements, each data element of the plurality of data elements including a first composite, a second composite, and a third composite, the first composite representing a condition of a patient, the second composite representing a severity of the condition, and the third composite representing an error rate corresponding to data associated with the condition of the patient represented by the first composite; and for a data stream of the one or more data streams:

parsing the data stream into one or more individual data elements, extracting information from a first composite, a second composite, and a third composite of an individual data element of the one or more individual data elements, identifying identify a patient communication device using the extracted information from the first composite and the second composite of the individual data element, each of the patient communication device and the individual data element being associated with a patient, the patient communication device being a computer, a mobile device, a smart phone, a laptop, an electronic badge, a set-top box, a thin client device, a tablet, or a pager, querying a lookup table using the second composite and the third composite, identifying a priority tag based on a result of the query, associating the priority tag to the individual data element, identifying a communication protocol associated with the priority tag, the communication protocol including a first communication trigger for a target task associated with the condition of the patient represented by the first composite, identifying a first navigator device based on the source data, the first navigator device being associated with a first calendar schedule of a nurse or a physician, automatically adjusting the first calendar schedule to include the first communication trigger, automatically determining a candidate time assignment to assign to the target task, each of the first composite and the second composite of the individual data element being used to automatically determine the candidate time assignment, and the candidate time assignment corresponding to a proposed appointment time for the patient, detecting that the first communication trigger has occurred based on the first calendar schedule, facilitating an initiation of a first communication attempt from the first navigator device to the patient communication device according to the first communication trigger, the first communication attempt including the candidate time assignment, and determining whether the initiation of the first communication attempt has occurred within a defined time period, wherein when the initiation of the first communication attempt has not occurred within the defined time period, a second calendar schedule associated with a second navigator device is automatically adjusted to include a second communication trigger for the target task, and the second navigator device initiates a second communication attempt from the second navigator device to the patient communication device, wherein if the error rate is greater than a threshold, the priority tag and the associated communication protocol indicate a high priority of facilitating the initiation of the first communication attempt from the first navigator device to the patient communication device, and the first communication attempt includes a follow-up to address the error rate.

9. The computer-implemented method for automatically adjusting calendar schedules to facilitate initiations of communication attempts with patient communication devices as recited in claim 8, further comprising:

adjusting the first calendar schedule associated with the first navigator device to include the target task.

10. The computer-implemented method for automatically adjusting calendar schedules to facilitate initiations of communication attempts with patient communication devices as recited in claim 8, wherein the second composite includes a representation of the first composite, the representation including additional information associated with the first composite.

11. The computer-implemented method for automatically adjusting calendar schedules to facilitate initiations of communication attempts with patient communication devices as recited in claim 8, further comprising:
when it is determined that the initiation of the first communication attempt has occurred, transmitting a confirmation communication to the patient communication device, the confirmation communication including information associated with the initiation of the first communication attempt; and
updating a record associated with the patient communication device with the information associated with the initiation of the first communication attempt.

12. The computer-implemented method for automatically adjusting calendar schedules to facilitate initiations of communication attempts with patient communication devices as recited in claim 8, further comprising:
when it is determined that the initiation of the first communication attempt has not occurred within the defined time period, identifying the second navigator device;
detecting that the second communication trigger has occurred; and
facilitating the second communication attempt with the patient communication device.

13. A non-transitory machine-readable storage medium, including instructions configured to cause a data processing apparatus to perform operations including:
receiving source data from one or more sources;
generating one or more data streams using the source data, each data stream of the one or more data streams including a plurality of data elements, each data element of the plurality of data elements including a first composite, a second composite, and a third composite, the first composite representing a condition of a patient, the second composite representing a severity of the condition, and the third composite representing an error rate corresponding to data associated with the condition of the patient represented by the first composite; and
for a data stream of the one or more data streams:
parsing the data stream into one or more individual data elements,
extracting information from a first composite, a second composite, and a third composite of an individual data element of the one or more individual data elements,
identifying identify a patient communication device using the extracted information from the first composite and the second composite of the individual data element, each of the patient communication device and the individual data element being associated with a patient, the patient communication device being a computer, a mobile device, a smart phone, a laptop, an electronic badge, a set-top box, a thin client device, a tablet, or a pager,
querying a lookup table using the second composite and the third composite,
identifying a priority tag based on a result of the query, associating the priority tag to the individual data element,
identifying a communication protocol associated with the priority tag, the communication protocol including a first communication trigger for a target task associated with the condition of the patient represented by the first composite,
identifying a first navigator device based on the source data, the first navigator device being associated with a first calendar schedule of a nurse or a physician,
automatically adjusting the first calendar schedule to include the first communication trigger,
automatically determining a candidate time assignment to assign to the target task, each of the first composite and the second composite of the individual data element being used to automatically determine the candidate time assignment, and the candidate time assignment corresponding to a proposed appointment time for the patient,
detecting that the first communication trigger has occurred based on the first calendar schedule,
facilitating an initiation of a first communication attempt from the first navigator device to the patient communication device according to the first communication trigger, the first communication attempt including the candidate time assignment, and
determining whether the initiation of the first communication attempt has occurred within a defined time period, wherein when the initiation of the first communication attempt has not occurred within the defined time period, a second calendar schedule associated with a second navigator device is automatically adjusted to include a second communication trigger for the target task, and the second navigator device initiates a second communication attempt from the second navigator device to the patient communication device,
wherein if the error rate is greater than a threshold, the priority tag and the associated communication protocol indicate a high priority of facilitating the initiation of the first communication attempt from the first navigator device to the patient communication device, and the first communication attempt includes a follow-up to address the error rate.

14. The non-transitory machine-readable storage medium as recited in claim 13, wherein the operations further comprise:
adjusting the first calendar schedule associated with the first navigator device to include the target task.

15. The non-transitory machine-readable storage medium as recited in claim 13, wherein the second composite includes a representation of the first composite, the representation including additional information associated with the first composite.

16. A system for automatically adjusting calendar schedules to facilitate initiations of communications with patient communication devices, the system comprising:
one or more data sources that transmit source data;
a stream processor that:
receives the source data, and
generates one or more data streams using the source data, each data stream of the one or more data streams including a plurality of data elements, each data element of the plurality of data elements including a first composite and a second composite, the first composite representing a condition of a patient and the second composite representing a severity of the condition; and a hospital communication server associated with a hospital facility, the hospital communication server being configured to, for a data stream of the one or more data streams:
  parse the data stream into one or more individual data elements,
  extract information from a first composite and a second composite of an individual data element of the one or more individual data elements,
  identify a patient communication device using the extracted information from the first composite and the second composite of the individual data element, each of the patient communication device and the individual data element being associated with a patient, the patient communication device being a computer, a mobile device, a smart phone, a laptop, an electronic badge, a set-top box, a thin client device, a tablet, or a pager,
  query a lookup table using the second composite,
  identify a priority tag based on a result of the query,
  associate the priority tag to the individual data element,
  identify a communication protocol associated with the priority tag, the communication protocol including a first communication trigger for a first target task associated with the condition of the patient represented by the first composite,
  identify a first navigator device based on the source data, the first navigator device being associated with a first calendar schedule of a nurse or a physician,
  automatically adjust the first calendar schedule to include the first communication trigger;
  automatically determine a first candidate time assignment to assign to the first target task, each of the first composite and the second composite of the individual data element being used to automatically determine the first candidate time assignment, and the first candidate time assignment corresponding to a first proposed appointment time for the patient,
  detect that the first communication trigger has occurred based on the first calendar schedule,
  facilitate an initiation of a first communication attempt from the first navigator device to the patient communication device according to the first communication trigger, the first communication attempt including the first candidate time assignment,
  determine whether the initiation of the first communication attempt has occurred within a defined time period, wherein when the initiation of the first communication attempt has not occurred within the defined time period, a second calendar schedule associated with a second navigator device is automatically adjusted to include a second communication trigger for the first target task, and the second navigator device initiates a second communication attempt from the second navigator device to the patient communication device, and
  automatically determine a plurality of additional candidate time assignments to assign to a plurality of additional target tasks associated with the condition of the patient represented by the first composite, each of the first composite and the second composite of the individual data element being used to automatically determine the plurality of additional candidate time assignments, and each of the additional candidate time assignments corresponding to a respective additional proposed appointment time for the patient,
  wherein the first communication attempt further includes the plurality of additional candidate time assignments, and
  wherein an order of the first candidate time assignment and the plurality of additional candidate time assignments is determined as a function of a sequence of the first target task and the plurality of additional target tasks to complete a program for treating the condition of the patient represented by the first composite.

17. The system for automatically adjusting calendar schedules to facilitate initiations of communications with patient communication devices as recited in claim 16, wherein the hospital communication server is further configured to:
  automatically determine that two or more of the plurality of additional target tasks are performable within a temporal window, and
  assign the two or more of the plurality of additional target tasks to one of the additional candidate time assignments.

18. A system for automatically adjusting calendar schedules to facilitate initiations of communications with patient communication devices, the system comprising:
  one or more data sources that transmit source data;
  a stream processor that:
    receives the source data, and
    generates one or more data streams using the source data, each data stream of the one or more data streams including a plurality of data elements, each data element of the plurality of data elements including a first composite and a second composite, the first composite representing a condition of a patient and the second composite representing a severity of the condition; and
  a hospital communication server associated with a hospital facility, the hospital communication server being configured to, for a data stream of the one or more data streams:
    parse the data stream into one or more individual data elements,
    extract information from a first composite and a second composite of an individual data element of the one or more individual data elements,
    identify a patient communication device using the extracted information from the first composite and the second composite of the individual data element, each of the patient communication device and the individual data element being associated with a patient, the patient communication device being a computer, a mobile device, a smart phone, a laptop, an electronic badge, a set-top box, a thin client device, a tablet, or a pager,
    query a lookup table using the second composite,
    identify a priority tag based on a result of the query,
    associate the priority tag to the individual data element,
    identify a communication protocol associated with the priority tag, the communication protocol including a first communication trigger for a first target task associated with the condition of the patient represented by the first composite,
    identify a first navigator device based on the source data, the first navigator device being associated with a first calendar schedule of a nurse or a physician,
    automatically adjust the first calendar schedule to include the first communication trigger;

automatically determine a first candidate time assignment to assign to the first target task, each of the first composite and the second composite of the individual data element being used to automatically determine the first candidate time assignment, and the first candidate time assignment corresponding to a first proposed appointment time for the patient, detect that the first communication trigger has occurred based on the first calendar schedule, facilitate an initiation of a first communication attempt from the first navigator device to the patient communication device according to the first communication trigger, the first communication attempt including the first candidate time assignment, determine whether the initiation of the first communication attempt has occurred within a defined time period, wherein when the initiation of the first communication attempt has not occurred within the defined time period, a second calendar schedule associated with a second navigator device is automatically adjusted to include a second communication trigger for the first target task, and the second navigator device initiates a second communication attempt from the second navigator device to the patient communication device, extract information from another first composite and another second composite of another individual data element of the one or more individual data elements, and automatically determine a plurality of additional candidate time assignments to assign to a plurality of additional target tasks associated with the condition of the patient represented by the first composite or the condition of the patient represented by the other first composite, each of the first composite and the second composite of the individual data element being used to automatically determine the plurality of additional candidate time assignments for the condition of the patient represented by the first composite, each of the other first composite and the other second composite of the other individual data element being used to automatically determine the plurality of additional candidate time assignments for the condition of the patient represented by the other first composite, and each of the additional candidate time assignments corresponding to a respective additional proposed appointment time for the patient, wherein the first communication attempt further includes the plurality of additional candidate time assignments, and wherein an order of the first candidate time assignment and the plurality of additional candidate time assignments is determined as a function of a relative priority of the condition of the patient represented by the first composite and the condition of the patient represented by the other first composite.

19. The system for automatically adjusting calendar schedules to facilitate initiations of communications with patient communication devices as recited in claim 18, wherein the hospital communication server is further configured to:

automatically determine that two or more of the plurality of additional target tasks are performable within a temporal window, and assign the two or more of the plurality of additional target tasks to one of the additional candidate time assignments.

20. A computer-implemented method for automatically adjusting calendar schedules to facilitate initiations of communication attempts with patient communication devices, comprising:

receiving source data from one or more sources;

generating one or more data streams using the source data, each data stream of the one or more data streams including a plurality of data elements, each data element of the plurality of data elements including a first composite and a second composite, the first composite representing a condition of a patient and the second composite representing a severity of the condition; and for a data stream of the one or more data streams:

parsing the data stream into one or more individual data elements, extracting information from a first composite and a second composite of an individual data element of the one or more individual data elements, identifying identify a patient communication device using the extracted information from the first composite and the second composite of the individual data element, each of the patient communication device and the individual data element being associated with a patient, the patient communication device being a computer, a mobile device, a smart phone, a laptop, an electronic badge, a set-top box, a thin client device, a tablet, or a pager, querying a lookup table using the second composite, identifying a priority tag based on a result of the query, associating the priority tag to the individual data element, identifying a communication protocol associated with the priority tag, the communication protocol including a first communication trigger for a first target task associated with the condition of the patient represented by the first composite, identifying a first navigator device based on the source data, the first navigator device being associated with a first calendar schedule of a nurse or a physician, automatically adjusting the first calendar schedule to include the first communication trigger, automatically determining a first candidate time assignment to assign to the first target task, each of the first composite and the second composite of the individual data element being used to automatically determine the first candidate time assignment, and the first candidate time assignment corresponding to a first proposed appointment time for the patient, detecting that the first communication trigger has occurred based on the first calendar schedule, facilitating an initiation of a first communication attempt from the first navigator device to the patient communication device according to the first communication trigger, the first communication attempt including the first candidate time assignment, determining whether the initiation of the first communication attempt has occurred within a defined time period, wherein when the initiation of the first communication attempt has not occurred within the defined time period, a second calendar schedule associated with a second navigator device is automatically adjusted to include a second communication trigger for the first target task, and the second navigator device initiates a second communication attempt from the second navigator device to the patient communication device, and automatically determining a plurality of additional candidate time assignments to assign to a plurality of additional target tasks associated with the condition of the patient represented by the first composite, each of the first composite and the second composite of the individual data element being used to automatically determine the plurality of additional candidate time assignments, and each of the additional candidate time assignments corresponding to a respective additional proposed appointment time for the patient, wherein the first communication attempt further includes the plurality of additional candidate time assignments, and wherein an order of the first candidate time assignment and the plurality of additional candidate time assignments is determined as a function of a sequence of the first target task and the plurality of additional target tasks to complete a program for treating the condition of the patient represented by the first composite.

* * * * *